(12) United States Patent
Solem et al.

(10) Patent No.: US 8,075,616 B2
(45) Date of Patent: Dec. 13, 2011

(54) APPARATUS FOR APPLYING A COMPRESSIVE LOAD ON BODY TISSUE

(75) Inventors: Jan Otto Solem, Stetten (CH); Per Ola Kimblad, Lund (SE); Randolf von Oepen, Los Altos Hills, CA (US); Bodo Quint, Rottenburg-Seebronn (SE); Gerd Seibold, Ammerbuch (SE); Kenneth J. Michlitsch, Livermore, CA (US); Suk-Woo Ha, Langwiesen (CH); Karl-Ludwig Eckert, Marthalen (CH); Ib Joergensen, Haigerloch (DE); Stevan Nielsen, Rottenburg (DE)

(73) Assignee: Edwards Lifesciences AG, Nyon (CH)

( * ) Notice: Subject to any disclaimer, the term of this patent is extended or adjusted under 35 U.S.C. 154(b) by 955 days.

(21) Appl. No.: 10/500,188

(22) PCT Filed: Dec. 20, 2002

(86) PCT No.: PCT/EP02/14655
§ 371 (c)(1),
(2), (4) Date: Nov. 22, 2004

(87) PCT Pub. No.: WO03/055417
PCT Pub. Date: Jul. 10, 2003

(65) Prior Publication Data
US 2005/0080483 A1    Apr. 14, 2005

Related U.S. Application Data

(63) Continuation-in-part of application No. 10/141,348, filed on May 9, 2002.

(60) Provisional application No. 60/344,121, filed on Dec. 28, 2001.

(30) Foreign Application Priority Data

Jan. 11, 2002    (SE) ..................................... 0200073

(51) Int. Cl.
*A61F 2/24*    (2006.01)
(52) U.S. Cl. ..................................................... 623/2.37
(58) Field of Classification Search ......... 623/1.11–1.54
See application file for complete search history.

(56) References Cited

U.S. PATENT DOCUMENTS 4,164,046 A    8/1979    Cooley
(Continued)

FOREIGN PATENT DOCUMENTS

DE    196 05 042 A1    1/1998
(Continued)

OTHER PUBLICATIONS

Laaksovirta et al., *Expansion and bioabsorption of the self-reinforced lactic and glycolic acid copolymer prostatic spiral stent*, PubMed, Excerpt from J Urol Sep. 2001; 166(3):919-22, one sheet.

(Continued)

*Primary Examiner* — David Isabella
*Assistant Examiner* — Ann Schillinger
(74) *Attorney, Agent, or Firm* — Melinda R. Michalerya

(57) ABSTRACT

A device for reshaping a cardiac valve (26), which is elongate and has such dimensions as to be insertable into a cardiac vessel (24). The device has two states, in a first state (K) of which the device has a shape that is adaptable to the shape of the vessel (24), and to the second state (k') of which the device is transferable from said first state (K). Further, the device comprises a fixing means (22,23;22a,23a) for fixing the ends of the device within the vessel (24), when the device is first positioned therein, a shape-changing member (20;20a) for transferring the device to the second state (K') by reshaping it, and a delay means (21;21a) for delaying said reshaping until the fixing of the ends of the device has been reinforced by keeping said device in said first state (K) until the delay means (21;21a) is resorbed.

8 Claims, 25 Drawing Sheets

U.S. PATENT DOCUMENTS

| | | | |
|---|---|---|---|
| 4,655,771 A | | 4/1987 | Wallsten |
| 4,877,030 A | * | 10/1989 | Beck et al. ..................... 606/195 |
| 4,954,126 A | | 9/1990 | Wallsten |
| 5,006,106 A | | 4/1991 | Angelchik |
| 5,061,275 A | | 10/1991 | Wallsten et al. |
| 5,064,435 A | | 11/1991 | Porter |
| 5,071,407 A | | 12/1991 | Termin et al. |
| 5,104,404 A | | 4/1992 | Wolff |
| 5,163,955 A | | 11/1992 | Love et al. |
| 5,170,802 A | | 12/1992 | Mehra |
| 5,209,730 A | | 5/1993 | Sullivan |
| 5,224,491 A | | 7/1993 | Mehra |
| 5,304,131 A | | 4/1994 | Paskar |
| 5,382,259 A | | 1/1995 | Phelps et al. |
| 5,383,892 A | | 1/1995 | Cardon et al. |
| 5,390,661 A | | 2/1995 | Griffith et al. |
| 5,441,515 A | | 8/1995 | Khosravi et al. |
| 5,449,373 A | | 9/1995 | Pinchasik et al. |
| 5,476,471 A | | 12/1995 | Shifrin et al. |
| 5,496,275 A | | 3/1996 | Sirhan et al. |
| 5,531,779 A | | 7/1996 | Dahl et al. |
| 5,534,007 A | | 7/1996 | St. Germain et al. |
| 5,545,209 A | | 8/1996 | Roberts et al. |
| 5,571,135 A | | 11/1996 | Fraser et al. |
| 5,575,771 A | * | 11/1996 | Walinsky ................... 604/96.01 |
| 5,584,879 A | | 12/1996 | Reimold et al. |
| 5,591,197 A | | 1/1997 | Orth et al. |
| 5,593,442 A | | 1/1997 | Klein |
| 5,607,444 A | * | 3/1997 | Lam ............... 606/194 |
| 5,674,280 A | | 10/1997 | Davidson et al. |
| 5,690,642 A | * | 11/1997 | Osborne et al. .............. 623/1.11 |
| 5,713,949 A | | 2/1998 | Jayaraman |
| 5,741,274 A | | 4/1998 | Lenker et al. |
| 5,817,126 A | | 10/1998 | Imran |
| 5,824,071 A | | 10/1998 | Nelson et al. |
| 5,876,419 A | | 3/1999 | Carpenter et al. |
| 5,876,433 A | | 3/1999 | Lunn |
| 5,891,108 A | | 4/1999 | Leone et al. |
| 5,911,732 A | | 6/1999 | Hojeibane |
| 5,919,233 A | | 7/1999 | Knopf et al. |
| 5,935,081 A | | 8/1999 | Kadhiresan |
| 5,954,761 A | | 9/1999 | Machek et al. |
| 5,961,545 A | | 10/1999 | Lentz et al. |
| 5,980,552 A | | 11/1999 | Pinchasik et al. |
| 6,006,122 A | | 12/1999 | Smits |
| 6,013,854 A | | 1/2000 | Moriuchi |
| 6,019,739 A | | 2/2000 | Rhee et al. |
| 6,027,525 A | | 2/2000 | Suh et al. |
| 6,051,020 A | | 4/2000 | Goicoechea et al. |
| 6,071,292 A | | 6/2000 | Makower et al. |
| 6,077,296 A | | 6/2000 | Shokoohi et al. |
| 6,093,203 A | | 7/2000 | Uflacker |
| 6,110,100 A | | 8/2000 | Talpade |
| 6,123,699 A | | 9/2000 | Webster, Jr. |
| 6,161,029 A | | 12/2000 | Spreigl et al. |
| 6,161,543 A | | 12/2000 | Cox et al. |
| 6,165,169 A | | 12/2000 | Panescu et al. |
| 6,168,619 B1 | | 1/2001 | Dinh et al. |
| 6,171,329 B1 | | 1/2001 | Shaw et al. |
| 6,183,411 B1 | | 2/2001 | Mortier et al. |
| 6,203,556 B1 | | 3/2001 | Evans et al. |
| 6,210,432 B1 | | 4/2001 | Solem et al. |
| 6,221,103 B1 | | 4/2001 | Melvin |
| 6,248,119 B1 | | 6/2001 | Solem |
| 6,250,308 B1 | | 6/2001 | Cox |
| 6,264,602 B1 | | 7/2001 | Mortier et al. |
| 6,264,691 B1 | | 7/2001 | Gabbay |
| 6,325,826 B1 | | 12/2001 | Vardi et al. |
| 6,343,605 B1 | | 2/2002 | Lafontaine |
| 6,350,277 B1 | | 2/2002 | Kocur |
| 6,368,348 B1 | | 4/2002 | Gabbay |
| 6,402,679 B1 | | 6/2002 | Mortier et al. |
| 6,402,680 B2 | | 6/2002 | Mortier et al. |
| 6,402,781 B1 | | 6/2002 | Langberg et al. |
| 6,409,760 B1 | | 6/2002 | Melvin |
| 6,537,314 B2 | | 3/2003 | Langberg et al. |
| 6,569,198 B1 | | 5/2003 | Wilson et al. |
| 6,626,899 B2 | | 9/2003 | Houser et al. |
| 6,629,534 B1 | | 10/2003 | St. Goar et al. |
| 6,656,221 B2 | | 12/2003 | Taylor et al. |
| 6,669,687 B1 | | 12/2003 | Saadat |
| 6,676,702 B2 | | 1/2004 | Mathis |
| 6,706,065 B2 | | 3/2004 | Langberg et al. |
| 6,709,456 B2 | | 3/2004 | Langberg et al. |
| 6,764,510 B2 | | 7/2004 | Vidlund et al. |
| 6,790,231 B2 | | 9/2004 | Liddicoat et al. |
| 6,797,001 B2 | | 9/2004 | Mathis et al. |
| 6,800,090 B2 | | 10/2004 | Alferness et al. |
| 6,810,882 B2 | | 11/2004 | Langberg et al. |
| 6,824,562 B2 | | 11/2004 | Mathis et al. |
| 6,890,353 B2 | | 5/2005 | Cohn et al. |
| 6,908,478 B2 | | 6/2005 | Alferness et al. |
| 6,989,028 B2 | | 1/2006 | Lashinski et al. |
| 6,997,951 B2 | | 2/2006 | Solem et al. |
| 7,011,682 B2 | | 3/2006 | Lashinski et al. |
| 7,090,695 B2 | | 8/2006 | Solem et al. |
| 2001/0018611 A1 | | 8/2001 | Solem et al. |
| 2001/0044568 A1 | | 11/2001 | Langberg et al. |
| 2002/0016628 A1 | | 2/2002 | Langberg et al. |
| 2002/0019660 A1 | | 2/2002 | Gianotti et al. |
| 2002/0022880 A1 | | 2/2002 | Melvin |
| 2002/0052638 A1 | * | 5/2002 | Zadno-Azizi .................. 623/1.2 |
| 2002/0087173 A1 | | 7/2002 | Alferness et al. |
| 2002/0103533 A1 | | 8/2002 | Langberg et al. |
| 2002/0111533 A1 | | 8/2002 | Melvin |
| 2002/0111647 A1 | | 8/2002 | Khairkhahan et al. |
| 2002/0124857 A1 | | 9/2002 | Schroeppel |
| 2002/0151961 A1 | | 10/2002 | Lashinski et al. |
| 2002/0183837 A1 | | 12/2002 | Streeter et al. |
| 2002/0183838 A1 | | 12/2002 | Liddicoat et al. |
| 2002/0183841 A1 | | 12/2002 | Cohn et al. |
| 2002/0188170 A1 | | 12/2002 | Santamore et al. |
| 2003/0078465 A1 | | 4/2003 | Pai et al. |
| 2003/0078654 A1 | | 4/2003 | Taylor et al. |
| 2003/0083538 A1 | | 5/2003 | Adams et al. |
| 2003/0105520 A1 | | 6/2003 | Alferness et al. |
| 2003/0120341 A1 | | 6/2003 | Shennib et al. |
| 2003/0130730 A1 | | 7/2003 | Cohn et al. |
| 2003/0135267 A1 | | 7/2003 | Solem et al. |
| 2003/0144697 A1 | | 7/2003 | Mathis et al. |
| 2004/0019377 A1 | | 1/2004 | Taylor et al. |
| 2004/0039443 A1 | | 2/2004 | Solem et al. |
| 2004/0102840 A1 | | 5/2004 | Solem et al. |
| 2004/0102841 A1 | | 5/2004 | Langberg et al. |
| 2004/0133192 A1 | | 7/2004 | Houser et al. |
| 2004/0153146 A1 | | 8/2004 | Lashinski et al. |
| 2004/0176840 A1 | | 9/2004 | Langberg et al. |
| 2004/0267358 A1 | | 12/2004 | Reitan |
| 2005/0043792 A1 | | 2/2005 | Solem et al. |
| 2005/0060030 A1 | | 3/2005 | Lashinski et al. |
| 2005/0096740 A1 | | 5/2005 | Langberg et al. |
| 2006/0116756 A1 | | 6/2006 | Solem et al. |
| 2006/0116757 A1 | | 6/2006 | Lashinski et al. |
| 2006/0184230 A1 | | 8/2006 | Solem |

FOREIGN PATENT DOCUMENTS

| | | |
|---|---|---|
| DE | 196 11 755 A1 | 2/1998 |
| EP | 0 727 239 A2 | 8/1996 |
| EP | 1279382 A1 | 1/2003 |
| WO | WO 95/16407 | 6/1995 |
| WO | WO 96/34211 | 10/1996 |
| WO | WO 96/40356 | 12/1996 |
| WO | WO 98/18411 | 5/1998 |
| WO | WO 98/51365 | 11/1998 |
| WO | WO 99/44534 | 9/1999 |
| WO | WO 99/53977 | 10/1999 |
| WO | WO 00/18320 | 4/2000 |
| WO | WO 00/41649 | 7/2000 |
| WO | WO 00/44313 A1 | 8/2000 |
| WO | WO 01/00111 A1 | 1/2001 |
| WO | WO 01/50985 A1 | 7/2001 |
| WO | WO 01/54618 A1 | 8/2001 |
| WO | WO 01/85061 A2 | 11/2001 |
| WO | WO 01/89426 A1 | 11/2001 |
| WO | WO 02/00099 A2 | 1/2002 |
| WO | WO 02/01999 A2 | 1/2002 |
| WO | WO 02/05888 A1 | 1/2002 |

| | | |
|---|---|---|
| WO | WO 02/34118 A2 | 5/2002 |
| WO | WO 02/053206 A2 | 7/2002 |
| WO | WO 02/060352 A1 | 8/2002 |
| WO | WO 02/062263 A2 | 8/2002 |
| WO | WO 02/062270 A1 | 8/2002 |
| WO | WO 02/062408 A2 | 8/2002 |
| WO | WO 02/076284 A2 | 10/2002 |
| WO | WO 02/078576 A2 | 10/2002 |
| WO | WO 02/096275 A2 | 12/2002 |
| WO | WO 03/037171 A2 | 5/2003 |
| WO | WO 2004/084746 A2 | 10/2004 |

OTHER PUBLICATIONS

Liu et al., *Sutural expansion osteogenesis for management of the bony-tissue defect in cleft palate repair: experimental studies in dogs*, PubMed, Excerpt from Plast Reconstr Surg May 2000; 105(6):2012-25; discussion 2026-7, two sheets.

Yoneyama et al., *Super-elastic property of Ti-Ni alloy for use in dentistry*, PubMed, Excerpt from Front Med Biol Eng 2000; 10(2):97-103, one sheet.

Kotian, *Shape memory effect and super elasticity it's dental applications*, PubMed, Excerpt from Indian J Dent Res Apr.-Jun. 2001; 12(2):101-4, one sheet.

Kuo et al., *The use of nickel-titanium alloy in orthopedic surgery in China*, PubMed, Excerpt from Orthopedics Jan. 1989; 12(1):111-6, one sheet.

Civjan et al., *Potential applications of certain nickel-titanium (nitinol) alloys*, PubMed, Excerpt from J Dent Res Jan.-Feb. 1975;54(1):89-96, one sheet.

Brennan, *Suite of Shape-Memory Polymers*, http:///pubs.acs.org/cen/topstory/7906notw1.html, News of the Week Materials, Feb. 5, 2001, vol. 79, No. 6, Cenear 79 6 pp. 5, ISSN 0009-2347, three sheets.

Stikeman, *Total Recall*, An MIT Enterprise Technology Review—Innovation, Jun. 2001, two sheets.

European Patent Office Office action dated Dec. 22, 2003 for Application No. 00 946 661.6-2310, 4 sheets.

Written Opinion dated Nov. 8, 2002 for International application No. PCT/EP01/10371, 14 sheets.

International Search Report dated Apr. 23, 2002 for International application No. PCT/EP01/10371, 4 sheets.

International Search Report dated Mar. 15, 2000 for National application No. SE 9902455-6, 3 sheets.

International Search Report dated Oct. 9, 2002 for National application No. SE 0200073-5, 5 sheets.

International Search Report dated Jun. 5, 2003 for International application No. PCT/EP 02/14655, 7 sheets.

Buchanan et al., Circumferential Suture of the Mitral Annulus for Correction of Mitral Regurgitation in Dogs, Veterinary Surgery, 27: 182-193, 1998.

Buchanan JW, Sammarco CD, Circumferential Suture of the Mitral Annulus for Correction of Mitral Regurgitation in Dogs, PubMed, Excerpt from Vet Surg May-Jun. 1998; 27(3): 183-93, abstract, one sheet.

European Search Report dated Mar. 9, 2010.

\* cited by examiner

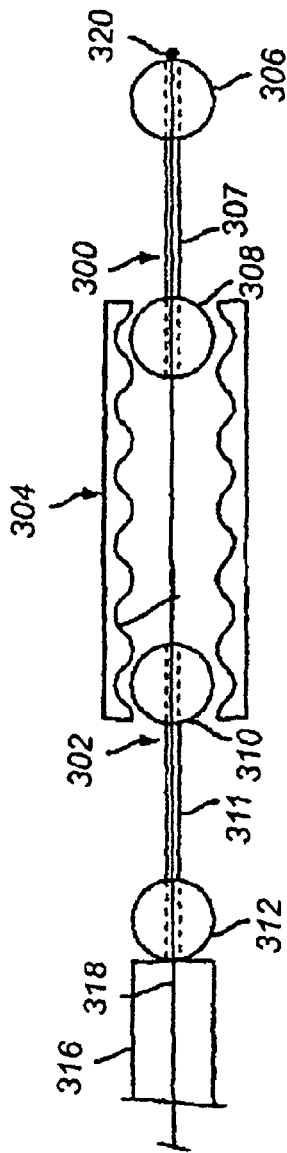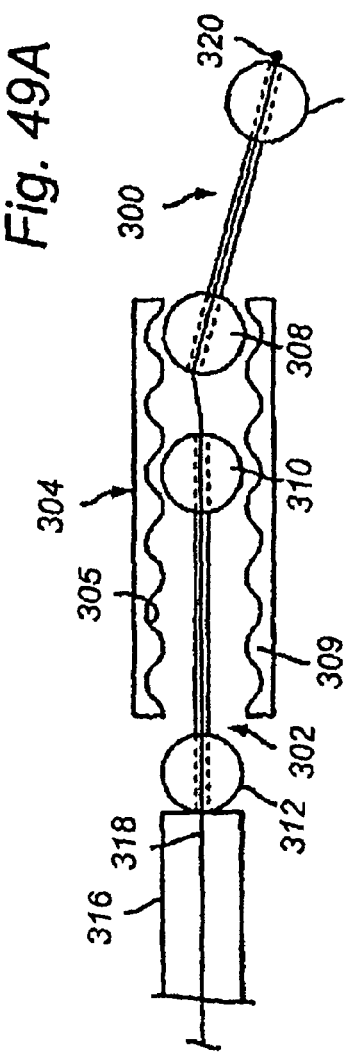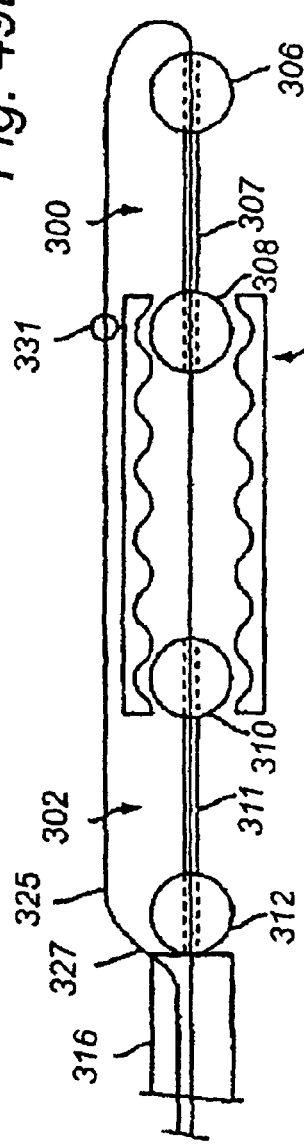

US 8,075,616 B2

APPARATUS FOR APPLYING A COMPRESSIVE LOAD ON BODY TISSUE

CROSS-REFERENCE TO RELATED APPLICATIONS

This application is a National Phase Application of International Application Number PCT/EP02/14655, filed Dec. 20, 2002 which claims priority to and is a continuation-in-part of U.S. application Ser. No. 10/141,348 filed on May 9, 2002, and claims priority to Swedish Application No. SE 0200073-5 filed Jan. 11, 2002, and Provisional Application No. 60/344,121 filed on Dec. 28, 2001.

TECHNICAL FIELD OF THE INVENTION

The present invention relates to a medical device and a method for reshaping a cardiac valve.

BACKGROUND OF THE INVENTION

Mitral insufficiency can result from several causes, such as ischemic disease, degenerative disease of the mitral apparatus, rheumatic fever, endocarditis, congenital heart disease and cardiomyopathy. The four major structural components of the mitral valve are the annulus, the two leaflets, the chordae and the papillary muscles. Any one or all of these in different combinations may be injured and create insufficiency. Annular dilation is a major component in the pathology of mitral insufficiency regardless of cause. Moreover, many patients have a mitral insufficiency primarily or exclusively due to posterior annular dilation, since the annulus of the anterior leaflet does not dilate because it is anchored to the fibrous skeleton of the base of the heart.

Studies of the natural history of mitral insufficiency have found that totally asymptomatic patients with severe mitral insufficiency usually progress to severe disability within five years. Currently, the treatment consists of either mitral valve replacements or repair, both methods requiring open heart surgery. Replacement can be performed with either mechanical or biological valves.

The mechanical valve carries the risk of thromboembolism and requires anticoagulation, with all its potential hazards, whereas biological prostheses suffer from limited durability. Another hazard with replacement is the risk of endocarditis. These risks and other valve related complications are greatly diminished with valve repair.

Mitral valve repair theoretically is possible if an essentially normal anterior leaflet is present. The basic four techniques of repair include the use of an annuloplasty ring, quadrangular segmental resection of diseased posterior leaflet, shortening of elongated chordae, and transposition of posterior leaflet chordae to the anterior leaflet.

Annuloplasty rings are needed to achieve a durable reduction of the annular dilation. All the common rings are sutured along the posterior mitral leaflet adjacent to the mitral annulus in the left atrium. The Duran ring encircles the valve completely, whereas the others are open towards the anterior leaflet. The ring can either be rigid, like the original Carpentier ring, or flexible but non-elastic, like the Duran ring or the Cosgrove-Edwards ring.

Effective treatment of mitral insufficiency currently requires open-heart surgery, by the use of total cardiopulmonary bypass, aortic cross-clamping and cardioplegic cardiac arrest. To certain groups of patients, this is particularly hazardous. Elderly patients, patients with a poor left ventricular function, renal disease, severe calcification of the aorta, and those having previous cardiac surgery or other concomitant diseases would in particular most likely benefit from a less invasive approach, even if repair is not complete.

Such a less invasive method is proposed in U.S. Pat. No. 6,210,432, which describes a method for treatment of mitral insufficiency without the need for cardiopulmonary by-pass and opening of the chest and heart. The method uses a device comprising an elongate body having such dimensions as to be insertable into the coronary sinus, which is a vein that substantially encircles the mitral orifice and annulus and drains blood from the myocardium to the right atrium. The elongate body has two states, in a first of which the elongate body has a shape that is adaptable to the shape of the coronary sinus, and to the second of which the elongate body is transferable from said first state assuming a reduced radius of curvature. Consequently, the radius of curvature of the coronary sinus is reduced. Due to the coronary sinus encircling the mitral annulus, the radius of curvature as well as the circumference of the mitral annulus are reduced. Thus, the described method takes advantage of the position of the coronary sinus being close to the mitral annulus, which makes repair possible by the use of current catheter-guided techniques.

According to one method described in U.S. Pat. No. 6,210,432, a device comprising an elongate stent is used. The elongate stent includes hooks which are arranged to dig into the walls of the coronary sinus, by means of the surgeon retracting a cover sheet from the stent, in order to fix the position of the stent in the coronary sinus. A stabilizing instrument is used for keeping the elongate stent in its first state and then, after the hooks have dug into the walls, releasing it to its second state assuming a reduced radius of curvature. However, the position fixation of the elongate stent in the coronary sinus by means of the hooks might be insufficient, so that the sudden release of the contraction of the elongate stent dislocates it. This dislocation of the device might result in unsatisfactory reduction of the circumference of the mitral annulus.

According to an alternative method described in U.S. Pat. No. 6,210,432 the device comprises three stent sections that are positioned in the coronary sinus and connected by wires. The wires may be maneuvered from outside the vein system such that the distances between the adjacent stent sections are reduced. Also with this method there is a risk of dislocation of the device, since the surgeon might accidentally move insufficiently fixed stent sections out of their proper position while manipulating them from outside the vein system.

In view of these drawbacks of previously known treatments, it would be desirable to provide a minimally invasive approach to treat mitral insufficiency, i.e., without the need for cardiopulmonary bypass and without opening of the chest and heart.

It also would be desirable to provide a reduction of the mitral annulus using only catheter based technology.

It further would be desirable to provide a treatment for mitral insufficiency that minimizes trauma to a patient's vasculature while using catheter based technology.

SUMMARY OF THE INVENTION

An object of the present invention is to provide an improved medical device and method for reshaping a cardiac valve, as described above.

A particular object of the invention is to provide a more secure fixation of a device for reshaping a cardiac valve.

It is another object of the present invention to provide a minimally invasive approach to treat mitral insufficiency, i.e., without the need for cardiopulmonary bypass and without opening of the chest and heart.

It is also an object of the present invention to provide a reduction of the mitral annulus using only catheter-based technology.

It is another object of the present invention to provide a treatment for mitral insufficiency that minimizes trauma to a patient's vasculature while using catheter based technology.

These and other objects of the present invention are achieved by providing a device for treatment of mitral insufficiency, whereby the circumference of the mitral valve annulus is reduced when the device is deployed and/or actuated in at least a portion of the coronary sinus.

More particularly, a device according to the present invention for reshaping a cardiac valve is elongate and has such dimensions as to be insertable into a cardiac vessel and has two states, in a first state of which the device has a shape that is adaptable to the shape of the vessel, and to the second state of which the device is transferable from said first state. The inventive device comprises a fixing means for fixing the ends of the device within the vessel, when the device is first positioned therein, a shape-changing member for transferring the device to the second state by reshaping it, and a delay means for delaying said reshaping until the fixing of the ends of the device has been reinforced, wherein said delay means delays said reshaping by keeping said device in said first state until the delay means is resorbed.

The delay means comprises a resorbable material, which is such material that when it is inserted into the body of an organism, it will be resorbed by the body by means of enzymatic processes, by active absorption by the cells in the blood and tissue cells of the body, and/or by hydrolysis. Thus, a resorbable material will be decomposed and gradually vanish from the device by time, without leaving any major waste products in the body.

When the device is inserted into the vessel, e.g. the coronary sinus, said fixing means provides for a "temporary" fixing of the ends of the device within the vessel. At the same time, said shape-changing member is e.g. by means of inherent forces of its material arranged to provide a change of shape of the device, and thereby also a change of shape of the adjacent cardiac valve. However, said delay means is arranged to delay this change of shape by keeping the device in said first state until the delay means is enough resorbed by the surrounding body. After some period of time, when there is nothing left of the delay means to hold the device in the first state, the fixing of the ends of the device will have had time to be reinforced by, for instance, the ends of the device having grown on to the vessel wall. The time period is thus determined by how fast the resorption of the delay means proceeds.

Hence, by delaying the change of shape this way, the device may be allowed to heal on to the vessel wall before the change of shape of the device occurs. The normal healing process that occurs in every living organism is thus allowed to provide a well-established fixation of the device. Hence, the present invention provides a more secure fixation of a device for reshaping a cardiac valve.

Another advantage of the present invention is that there is no need for a stabilizing surgical instrument for keeping the device in said first state of shape during operation, since the shape is preserved by means of said delay means of the device.

Preferably, said delay means comprises a resorbable sheath being arranged to enclose said shape-changing member. This is advantageous since with the shape of a sheath the delay means is both easy to manufacture and easy to arrange on the shape-changing member.

In another preferred embodiment of the invention, said fixing means is arranged to expand against the wall of the vessel when first positioned therein. This expansion against the wall of the vessel initiates and contributes to the fixing of the ends of the device, thus providing said "temporary" fixing of the ends of the device within the vessel and enabling a more rigid fixing by ingrowth.

In yet another preferred embodiment of the invention, said fixing means is arranged to grow into the wall of the vessel, whereby said fixing of the ends of the device is reinforced. Hence, by taking advantage of the healing process in the tissue of the vessel wall, the fixing means can be fixed effectively. This can be facilitated by an expansion against the wall of the vessel as mentioned above.

In a preferred embodiment, said fixing means comprises hook means, by means of which said fixing of the ends of the device is reinforced. These hook means may be combined with the above-mentioned ingrowth of the fixing means in order to provide an even more secure fixation. The hook means may dig into the vessel wall and grow firmly fixed in the wall by the healing process.

In another preferred embodiment, said fixing means comprises a self-expandable stent at each end of the device.

According to another preferred embodiment, said shape-changing member comprises a shape memory material providing said reshaping of the device. A shape memory material is a material that has two different forms, one at lower temperatures and another at higher temperatures. At the lower temperatures, e.g. below 30° C., the material is elastic and may be introduced into the body. At the higher temperatures, the material is still elastic but becomes also superelastic and assumes its preferred original shape unless the transformation to this original shape is obstructed by external stress to the material. The use of a shape memory material in the shape-changing member is advantageous inter alia because then one can easily provide the device with said delay means while the shape-changing member, at a lower temperature outside the body, more easily remains in a shape corresponding to said non-preferred state of shape inside the body.

In one embodiment of the invention, said shape-changing member comprises a shape memory metal providing said reshaping of the device.

Preferably, said shape-changing member comprises Nitinol.

In an alternative embodiment of the invention, said shape-changing member comprises a shape memory polymer.

Preferably, said reshaping of said device comprises shortening of said device.

In another preferred embodiment, said device is used for treatment of mitral annulus dilatation. Since the device can be inserted into a body vessel using catheter-guided techniques, the use of this device for treatment of mitral annulus dilatation is advantageous compared to open-heart surgery, which is the present procedure for repairing or replacing the mitral valve.

In yet another preferred embodiment, said vessel is the coronary sinus. The coronary sinus encircles the mitral orifice and annulus. Therefore, a reshaping of this vein also has a compressing effect on the mitral annulus.

Preferably, said reshaping of said device is used for reducing the radius of curvature of the coronary sinus. Hence, the radius of curvature as well as the circumference of the mitral annulus are also reduced.

According to the invention, a method for reshaping a cardiac valve, comprises the steps of inserting an elongate device into a cardiac vessel, fixing the ends of the device within the vessel, reinforcing said fixing of the ends of the device, reshaping the device, and delaying said reshaping by a delay means so that the step of reinforcing said fixing is performed before the step of reshaping the device.

According to a preferred embodiment, said step of fixing the ends of the device comprises providing a growth of the ends into the wall of the vessel.

According to another preferred embodiment, a shape memory material is used in the device for said step of reshaping the device.

Preferably, Nitinol is used in the device for said step of reshaping the device.

In a preferred embodiment, said step of reshaping the device comprises the step of shortening the device.

In another preferred embodiment, the method is used for treatment of mitral annulus dilatation.

In yet another preferred embodiment, said device is inserted into the coronary sinus in the vicinity of the posterior leaflet of the mitral valve.

Preferably, said reshaping is used for reducing the curvature of the coronary sinus and thereby reducing the radius of circumference of the mitral valve annulus.

The device in accordance with principles of the present invention may further comprise one or more components suitable for deployment in the coronary sinus and adjoining coronary veins. The device may be configured to bend in-situ to apply a compressive load to the mitral valve annulus with or without a length change, or may include multiple components that are drawn or contracted towards one another to reduce the circumference of the mitral valve annulus. Any of a number of types of anchors may be used to engage the surrounding vein and tissue, including hooks, barbs, flanges, partial or completely through-wall tee structures, or biological anchoring. Where multiple components are provided, reduction of the mitral valve annulus may be accomplished during initial deployment of the device, or by biological actuation during subsequent in-dwelling of the device.

In one embodiment comprising multiple components, the device comprises proximal and distal stent sections, wherein the proximal stent section comprises a deployable flange. The stent sections are delivered into the coronary sinus in a contracted state, and then are deployed within the coronary venous vasculature so that the flange engages the coronary sinus ostium. A cinch mechanism, comprising, for example, a plurality of wires and eyelets, is provided to reduce the distance between proximal and distal stent sections, thereby reducing the circumference of the mitral valve annulus.

In an alternative embodiment, the distal stent is replaced by or includes a suitably-shaped distal anchor that is disposed within or through the left ventricular myocardium. The distal anchor may be in the form of a Tee-shape or barbed section, and engages the ventricular myocardium, or extends into the left ventricle, to provide a distal fixation point. As in the preceding embodiment, a cinch mechanism is provided to shorten a structure, such as a wire, that extends between the proximal stent and the distal anchor. The distal anchor may be used alone or in conjunction with the proximal flange of the preceding embodiment.

In a further alternative embodiment, a balloon catheter is used wherein a balloon in fluid communication with a lumen of the catheter comprises a predetermined deployed shape. A stent, which may be compressed onto the balloon in a contracted state, then is plastically deformed by the balloon within the coronary sinus, and the stent substantially conforms to the predetermined shape of the balloon in a deployed state. The balloon preferably comprises a convex shape, so that the stent will assume the convex shape of the balloon and bend the coronary sinus accordingly. The shape of the stent, convex or otherwise, will be configured to reduce the circumference of the mitral valve annulus when deployed in the coronary sinus.

In a yet further embodiment, the proximal and distal stent sections are directly coupled to one another by a central section, so that expansion of the central section causes the proximal and distal stent sections to be drawn together. In this embodiment, however, the central section includes one or more biodegradable structures, such as biodegradable sutures, that retain the central section in its contracted state until the vessel endothelium has overgrown a portion of the proximal and distal stent sections, thereby providing biological anchoring of the proximal and distal stent sections. After the proximal and distal stent sections have become endothelialized, the biodegradable structure degrades, releasing the central section and enabling it to expand. The central section thereby applies a tensile load to the proximal and distal stent sections, causing a reduction in the circumference of the mitral valve annulus.

A yet further alternative embodiment comprises a series of linked segments that are capable of relative rotational and telescoping movement. In a preferred embodiment, each segment includes a ball element that couples to a socket element on an adjacent segment. The ball and socket connections permit the segments of the device to become angled relative to one another so that the device is capable of assuming a three-dimensional curvature. A cinch wire extends through a passage in the segments and permits the device to be cinched rigidly into a predetermined shape. Some segments also may include telescoping joints that permit the overall length of the device to be reduced upon actuation of the cinch wire. The cinch wire may include either a locking mechanism attached to the cinch wire or alternatively may include striations on the contacting ball and socket surfaces that permit the segments to rigidly engage one another when cinched.

BRIEF DESCRIPTION OF THE DRAWINGS

The invention will now be described in more detail with reference to the accompanying drawings, in which FIGS. 1 and 2 schematically illustrate an embodiment of a device according to the invention for reshaping a cardiac valve, shown in a first state and a second shortened state, respectively;

FIG. 21 is a schematic view illustrating the second state of a device according to FIG. 19 or 20a;

FIGS. 48A-50 illustrate a still further alternative embodiment of the present invention comprising a plurality of interconnected segments and deployment thereof.

DETAILED DESCRIPTION OF PREFERRED EMBODIMENTS

The present invention takes advantage of the position of the coronary sinus being close to the mitral annulus. This makes repair possible by the use of current catheter-guided techniques by deploying one element in the coronary venous vasculature that applies a load to, and reshapes, the adjacent posterior portion of the mitral annulus.

The coronary veins drain blood from the myocardium to the right atrium. The smaller veins drain blood directly into the atrial cavity, and the larger veins accompany the major arteries and run into the coronary sinus which substantially encircles the mitral orifice and annulus. The coronary sinus runs in the posterior atrioventricular groove, lying in the fatty tissue between the left atrial wall and the ventricular myocardium, before draining into the right atrium between the atrial septum and the post-Eustachian sinus.

Figure 1:
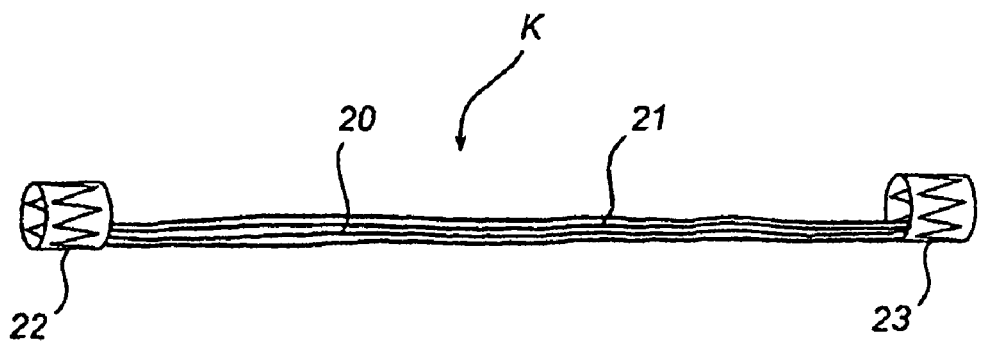
FIGS. 1a and 2a schematically illustrate another embodiment of a device according to the invention for reshaping a cardiac valve, shown in a first state and a second shortened state, respectively.

FIG. 1 shows one embodiment of a device according to the present invention for reshaping a cardiac valve, which may be used for treatment of mitral annulus dilatation.

The device shown in FIG. 1, being in an elongate and non-activated state of shape K, comprises a shape-changing member in the form of a shape memory metal thread 20, a delay means in the form of a resorbable sheath 21 enclosing the shape memory metal thread 20 for holding it in a straightened state of shape, and preferably self-expandable stents 22 and 23 located at the opposite ends of the device.

The device may include one or more additional shape memory metal threads, e.g. if a stronger shortening force is desired.

Figure 2:
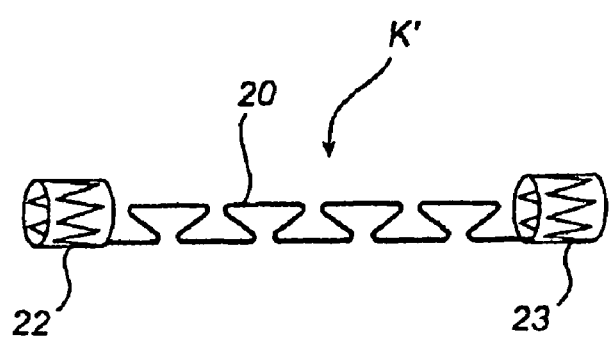

The shape-changing member, in this embodiment in the form of the shape memory metal thread 20, may consist of or at least include Nitinol, or some other similar material which has a memory of an original shape as illustrated in FIG. 2, and can be temporarily forced into another shape, e.g. as illustrated in FIG. 1. Nitinol is an alloy composed of nickel (54-60%) and titanium. Small traces of chromium, cobalt, magnesium and iron may also be present in Nitinol.

However, the material of the shape-changing member does not have to be a metal. Other materials such as Shape Memory Polymers (SMP) could be used as shape memory material as well.

Actually, as far as the present invention concerns, the shape-changing material does not have to be a shape memory material. Any superelastic material would function in most cases. For example stainless steel (and other metals) may also be forced into a non-preferred state of shape by means of a resorbable restraining means.

The delay means is in this embodiment in the form of the resorbable sheath 21. This resorbable sheath 21 is made of a material which is resorbable by the surrounding blood and tissue when applied in a human body and has the required stability and bending properties. Examples of usable resorbable materials from which the delay means may be made, or that are at least included, are PDS (polydioxanon), Pronova (polyhexaflouropropylen-VDF), Maxon (polyglyconat), Dexon (PGA, polyglycolic acid), Vicryl (polyglactin), PLA (polylactic acid), PDLLA (polydexolactic acid), PLLA (pololevolactic acid), starch, different kinds of sugar, butyric acid, collagen, and collatamp.

Depending on the choice of material, the release of the shape-changing forces of the shape-changing member may be delayed for a desired period of time. Also design parameters such as the thickness of the resorbable material may be set so that the change of shape is delayed as long as desired. The delay time may vary from e.g. a few days up to several years depending on the application.

The thickness of the delay means is chosen so that the time needed for the surrounding blood and tissue in the coronary sinus 24 to resorb the delay means enough for the device to enter its second shorter state of shape K' is adapted to the time needed for the ends of the device to be fixed within the coronary sinus 24.

The thickness of the delay means may vary along the device, so that the order in which different parts of the device are released by the delay means may be controlled.

The delay means may be flexible enough to follow the curves in e.g. a vessel, but has a stiffness, here especially in its radial direction, which withstands the shape-changing force of the shape-changing member. Thus, having been implanted into the human body, the shape-changing member of the device will strive towards its original, here curved, shape according to FIG. 2, but is restrained by the delay means.

The self-expandable stents 22 and 23 may be of conventional type with an elastic cylindrical unit, made of e.g. Nitinol, in an opened zigzag configuration.

The self-expandable stents 22 and 23 may be provided with hook means (not shown), in the form of protrusions extending from the outer surface of the stents 22 and 23. These hook means are arranged to dig into the wall of the coronary sinus 24 when the self-expandable stents 22 and 23 expand against the wall, and thereby facilitate and enhance the fixing of the self-expandable stents 22 and 23 into the wall of the coronary sinus 24.

Figure 1A:
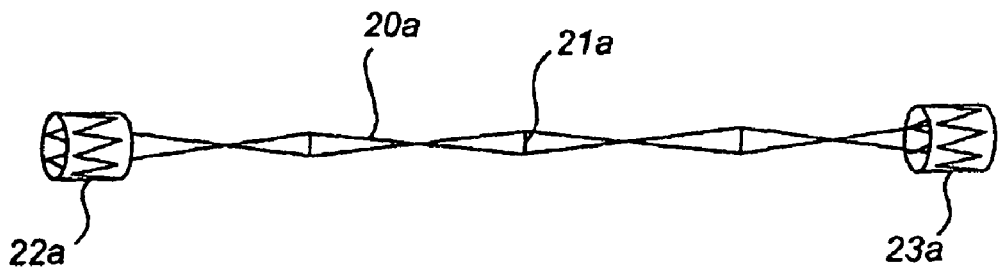
Figure 2A:
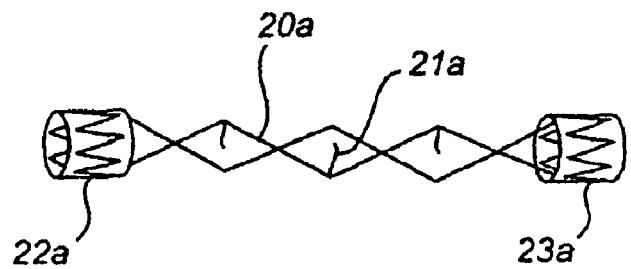

FIG. 1*a* shows an alternative embodiment according to the invention of a device for reshaping a cardiac valve. Here, the shape memory metal thread 20 is replaced by a scissors-shaped shape-changing member 20*a*. The resorbable sheath 21 may then be replaced by resorbable threads 21*a*. Preferably, self-expandable stents 22*a* and 23*a* are located at the opposite ends of the device. The state of shape corresponding to K' in FIG. 2 of the device shown in FIG. 1*a* is shown in FIG. 2*a*.

Figure 3:
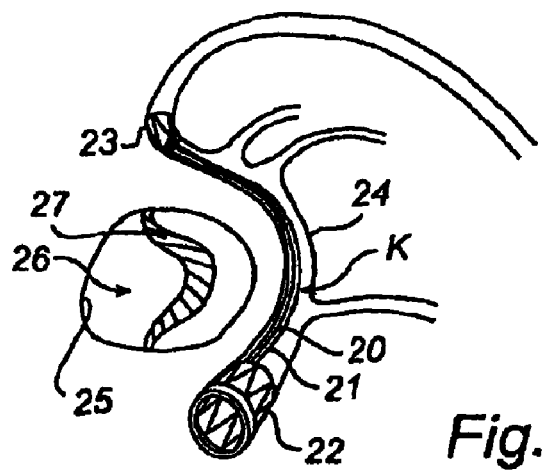
FIGS. 3, 4 and 5 are schematic views illustrating the positioning, the fixing and the shortening respectively, of a device according to FIG. 1 when used in the coronary sinus.

The above-described device as seen in FIG. 1 (or the device as seen in FIG. 1*a*), is positioned in the coronary sinus 24, shown in FIGS. 3 to 5, in the following way:

An introduction sheath (not shown) of synthetic material may be used to get access to the venous system. Having reached the venous system, a long guiding metal wire (not shown) is advanced through the introduction sheath and via the venous system to the coronary sinus 24. This guiding wire and/or a delivery catheter is provided with X-ray distance markers so that the position of the device in the coronary sinus 24 may be monitored.

The elongate device in FIG. 1 (or the one in FIG. 1*a*) is locked onto a stent insertion device (not shown) so that the self-expandable stents 22 and 23 (or 22*a* and 23*a*) are held in a crimped, non-expanded state. Thereafter, the stent insertion device with the elongate device locked thereon is pushed through the introduction sheath and the venous system to the coronary sinus 24 riding on the guiding wire. After having obtained an exact positioning of the elongate device in the coronary sinus 24, as illustrated in FIG. 3 where the mitral valve annulus 25 and the mitral valve 26 having a central gap 27 are shown, the stent insertion device is removed. This will release the self-expandable stents 22 and 23 (or 22*a* and 23*a*) so that they expand and contact the inner wall of the coronary sinus 24 and thereby provide for a temporary fixation of the elongate device in the coronary sinus 24. Then, the guiding wire and the introduction sheath are removed.

Figure 4:
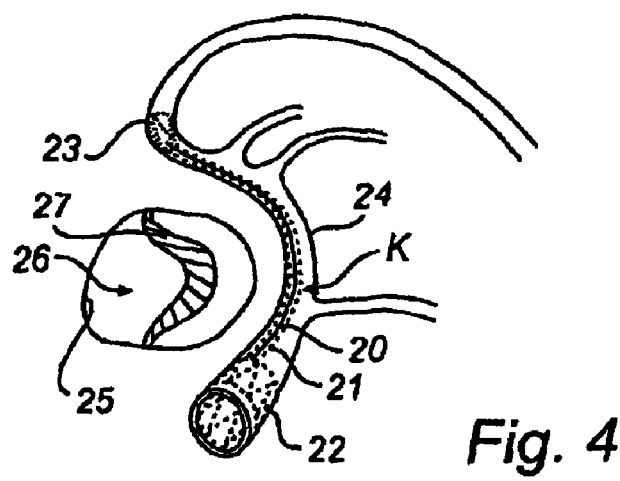
Figure 5:
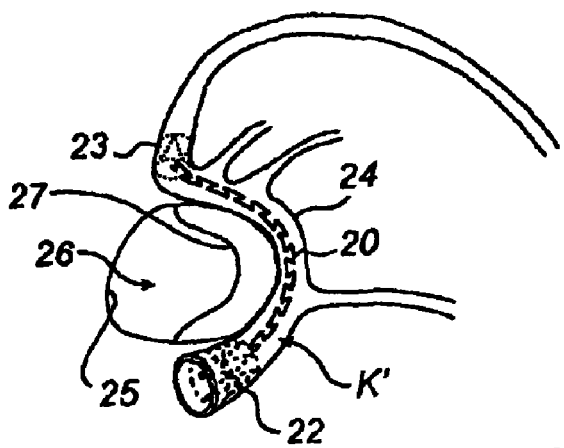

After the insertion, the self-expandable stents 22 and 23 (or 22*a* and 23*a*) will grow into the wall of the coronary sinus 24 while at the same time the resorbable sheath 21 (or restraining threads 21*a*) will be resorbed by the surrounding blood and tissue in the coronary sinus 24, as schematically illustrated in FIG. 4. When the resorbable sheath 21 (or resorbable threads 21*a*) has been resorbed to such a degree that it cannot hold the shape memory metal thread 20 (or the scissors-shaped member 20*a*) in its straightened state of shape any longer, the self-expandable stents 22 and 23 (or 22*a* and 23*a*) will be properly fixed into the wall of the coronary sinus 24 as a result of the normal healing process which always occurs after positioning a stent in a blood vessel. Then the shape memory metal thread 20 (or the scissors-shaped member 20*a*) retracts and the device is transformed to its activated shorter state of shape K', as illustrated in FIGS. 2 and 5 (corresponding to FIG. 2*a*). This shortening of the device makes it bend towards the mitral valve annulus 25, moving the posterior part thereof forward. This movement reduces the circumference of the mitral valve annulus 25 and thereby closes the central gap 27.

The device may be positioned by catheter technique or by any other adequate technique. It may be heparin-coated so as to avoid thrombosis in the coronary sinus 24, thus reducing the need for aspirin, ticlopedine or anticoagulant therapy. At least parts of the device may contain or be covered with drugs like Tacrolimus, Rappamycin or Taxiferol to be delivered into the tissue to prohibit excessive reaction from surrounding tissue. At least parts of the device may be covered with or contain VEGF (Vascular Endothelial Growth Factor) to ensure smooth coverage with endothelial cells.

It is to be understood that modifications of the above described devices and methods can be made by people skilled in the art without departing from the spirit and scope of the invention, which is only limited by the appended claims. For instance, the activated state of shape K' could be a bended shape instead of a shorter shape, whereby the desired closure of the central gap 27 still may be achieved.

The basic inventive idea of the present invention, which solves the problem with insufficient fixing of the implantable device before the shape of it is changed, is to delay the reshaping of the device by means of a (resorbable) delay means being comprised in the device itself, and thereby allow the device to grow fixed in body tissue by means of natural healing processes.

As far as the present invention concerns, it has been thoroughly disclosed above. However, during the progress of the invention, ideas came up to use the basic inventive idea not only for reshaping of a cardiac valve, but also for other non-related medical applications. Therefore, in the following there will be described examples of implantable devices embodying the basic inventive idea in different ways as regards construction and especially as regards the type of change of shape. Further, in the following, there will also be described examples of applications for which the basic inventive idea may be advantageously used. Some of the following description is applicable on the present invention, e.g. FIGS. 6 to 9 and FIGS. 15, 16, 15*a* and 16*a*, whereas some of it is not.

FIGS. 6 to 9 show the principle of delayed shortening.

Figure 6:
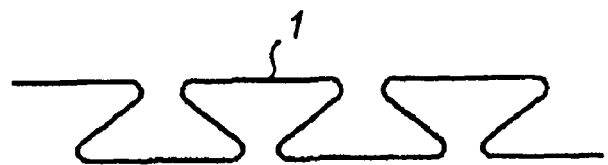
FIGS. 6-9 are schematic views of a device illustrating the principle of delayed shortening.

In FIG. 6, a shape-changing member 1, here in the form of a thread 1, made of or at least in part including a shape memory material is shown having a curved shape. This shape is the original shape that the shape-changing member 1 "remembers" and will assume when the temperature thereof passes a certain threshold, e.g. exceeds 30° C.

Figure 7:

FIG. 7 shows the shape-changing member 1 of FIG. 6 having been straightened by stretching to a substantially straight shape.

Figure 8:
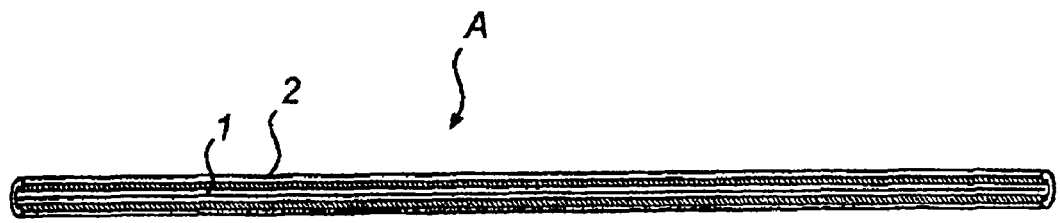

FIG. 8 illustrates a device which is in its non-activated state of shape A. More specifically, by covering the stretched and straight shape-changing member 1 in FIG. 7 with a delay means 2, here in the form of a tube 2 having a sufficiently small inner cross-section, the stretched shape of the shape-changing member 1 can be maintained even when the device is implanted into a human body and the temperature of the shape-changing member 1 thus exceeds the threshold, e.g. 30° C.

Figure 9:
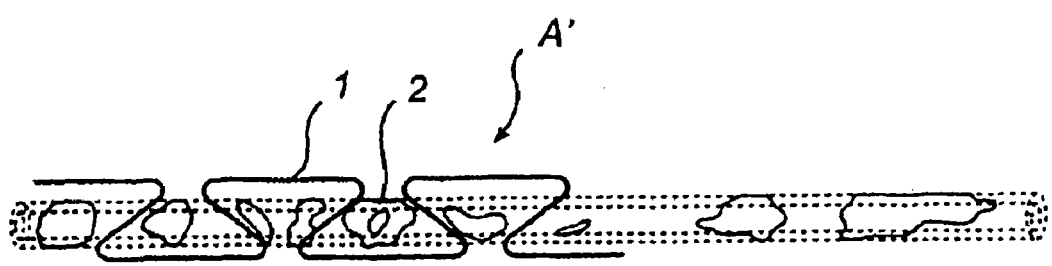

By manufacturing the delay means 2 from a resorbable material, the delay means 2 will be resorbed by time and the shape-changing member 1 will resume its original shape when the delay means 2 has been resorbed to such a degree or extent that it cannot restrain the shape-changing member 1 any longer, as schematically illustrated in FIG. 9. Thus, the device has now "been transformed" from its non-activated long state of shape A (FIG. 8), to an activated, shortened state of shape A' (FIG. 9), where the device consists essentially of the shape-changing member 1 only.

In order to clearly illustrate the shortening of the device, the curved thread 1 is located to the left in FIG. 9, but, after its transformation, the thread 1 may just as well be located anywhere along the remaining parts of the tube 2.

The device in FIG. 8 may be manufactured in the following way, which is also applicable for manufacturing all except the ends of the embodiment of a device according to the present invention shown in FIG. 1. The thread 1 of a shape memory material, e.g. with the shape illustrated in FIG. 7, is programmed to remember the shape illustrated in FIG. 6 by being held in that shape while at the same time being heated to a temperature above said threshold. Upon cooling, beneath the threshold temperature, e.g. down to room temperature, the thread 1 will become more flexible and may more easily be deformed into its previous shape shown in FIG. 7. In this cooled state, the thread 1 is covered by the resorbable tube 2, e.g. by threading the tube 2 onto the thread 1 or by forming the tube 2 around the thread 1.

Other devices according to the basic inventive idea, including embodiments of the present invention, may operate and may be manufactured in a corresponding manner. Thus, a shape-changing member of a memory material is first held in a "preferred" state of shape while being heated above a threshold temperature, and then cooled beneath the threshold temperature so that it can easily be deformed into its previous "non-preferred" state of shape. Thereafter, the now "programmed" shape-changing member is "locked" in said non-preferred state of shape by a delay means in such a way that the delay means will obstruct the shape-changing member from resuming its preferred state of shape when being heated again, e.g. in a human body. Referring again to FIG. 8, the inner radius of the tube 2 must not necessarily be so small that the shape-changing member in the form of the thread 1 cannot move at all in the radial direction. Hence, there may be a small radial play in which the shape-changing member 1 can move without consequently being able to change the length of the device to any larger extent. However, the device in FIG. 8 may also be manufactured with essentially no play between the shape-changing member 1 and the inner side of the delay means 2, possibly also with a pretension or bias force from the delay means 2 acting on the shape-changing member 1.

In FIGS. 10 to 13, the principle of delayed elongation is shown.

Figure 10:
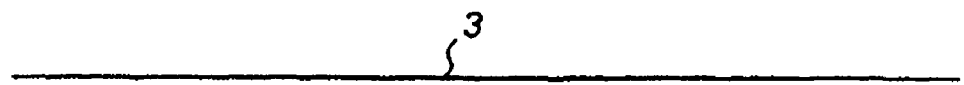
FIGS. 10-13 are schematic views of a device illustrating the principle of delayed elongation.

FIG. 10 shows a shape-changing member 3, here in the form of a thread 3 of a shape-memory material, having a straight original shape.

Figure 11:
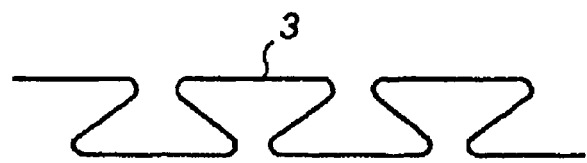

FIG. 11 shows the shape-changing thread member 3 of FIG. 10 when having been folded to a curved shape.

Figure 12:
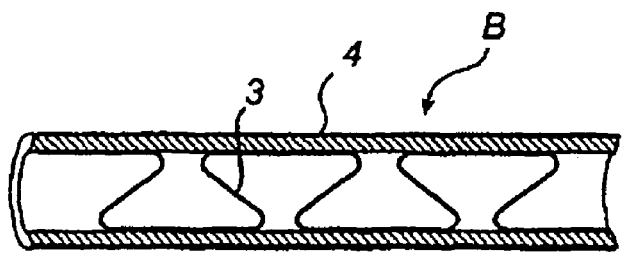

FIG. 12 illustrates a device according to the basic inventive idea comprising a thread 3 as illustrated in FIG. 11, where the device is in its non-activated state of shape B. By covering the curved shape-changing member 3 with a delay means 4 in the form of a tube 4 of a resorbable material, the curved shape B can be maintained even when the device is implanted into a human body and strives towards its original straight shape.

Figure 13:
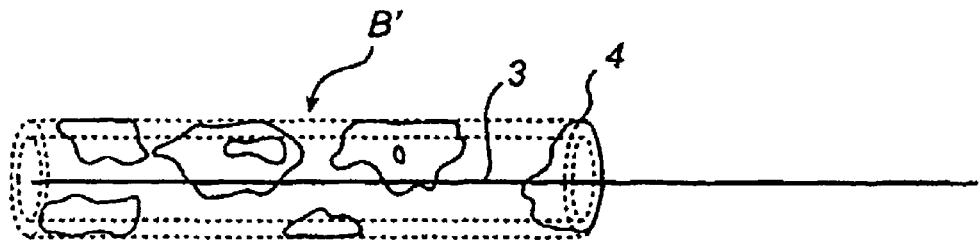

As schematically illustrated in FIG. 13, after implantation into the human body, the delay means 4 is resorbed by time and consequently the shape-changing member 3 will be released to resume its original straight shape B'. Thus, the device has now been transformed from its non-activated short state of shape B (FIG. 12) to an activated, elongated state of shape B' (FIG. 13).

In the illustrated devices, the length of the shape-changing member 1;3 is substantially unchanged by the transformation, whereas the shape of the shape-changing member 1;3 is changed so that the length of the device is changed.

FIGS. 14 to 25 show some different devices according to the basic inventive idea.

Figure 14:
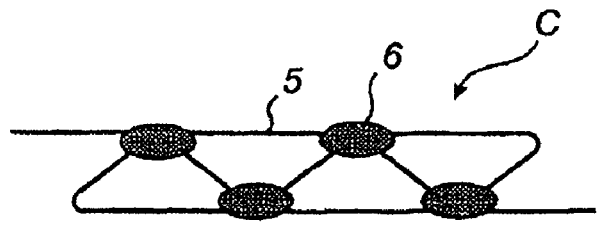
FIG. 14 is a schematic view showing an alternative to the device shown in FIG. 12.

FIG. 14 shows a device being an alternative arrangement of a device for delayed elongation as compared to the device shown in FIG. 12. Instead of a resorbable tube 4 as in FIG. 12, the delay means comprises resorbable crosslinks 6 which hold the shape-changing member 5 in its curved state of shape and thus the device in its non-activated short state of shape C.

Resorbable crosslinks 6 (FIG. 14) may also be combined with a tube 4 (FIG. 12).

Figure 15:
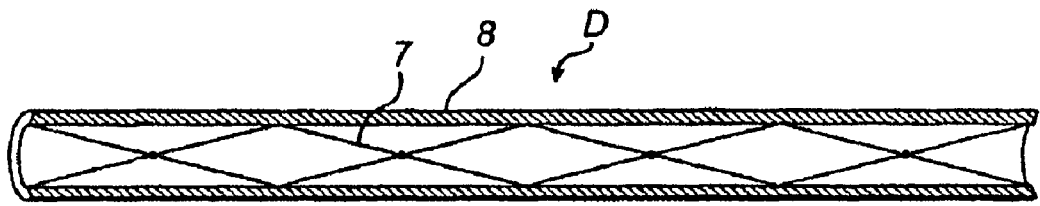
FIGS. 15 and 16 schematically illustrate another device, shown in a first state and a second shortened state, respectively.
Figure 16:
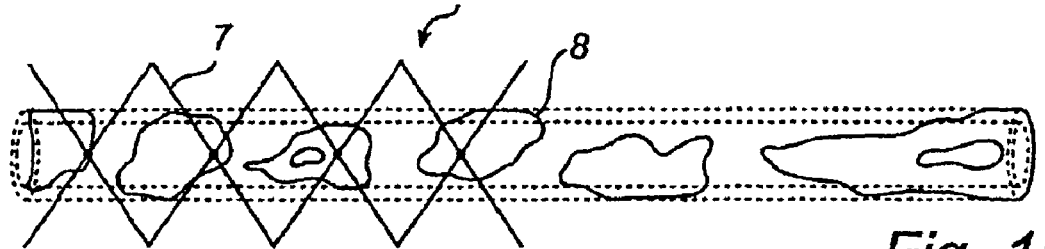

FIG. 15 shows a device in its non-activated elongate state of shape D. Here, the shape-changing member 7 is scissors-shaped. A delay means 8 in the form of a tube 8 of resorbable material holds the shape-changing member 7 in a stretched, elongated state of shape and, thus, also the device in its elongate state of shape D. When the delay means 8 has been sufficiently resorbed, the scissors-shaped shape-changing member 7 will resume its original non-stretched shape and the device is transformed to its activated short state of shape D' (FIG. 16).

Figure 15A:
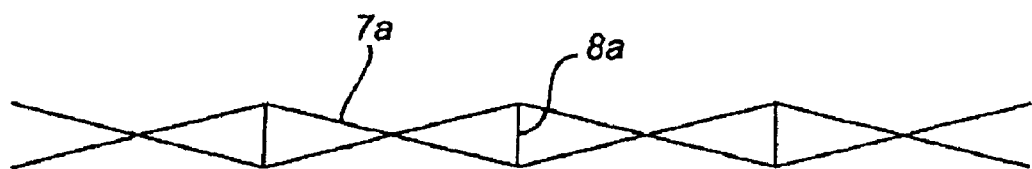
FIGS. 15a and 16a schematically illustrate an alternative to the device shown in FIGS. 15 and 16, wherein a delay means is provided in the form of resorbable threads.
Figure 16A:
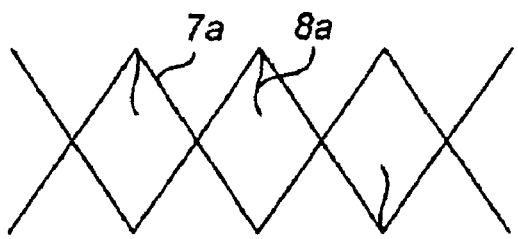

FIG. 15a shows an alternative device where the tube 8 in FIG. 15 is replaced by a delay means in the form of resorbable threads 8a. The delay means 8a holds the scissors-shaped shape-changing member 7a in a stretched, elongate state of shape and, thus, the device in a state of shape corresponding to D in FIG. 15. Referring to FIG. 16a, when the delay means 8a is cut off by means of resorption, the shape-changing member 7a will resume its original non-stretched shape and the device is transformed to its activated short state of shape corresponding to D' in FIG. 16.

Figure 17:
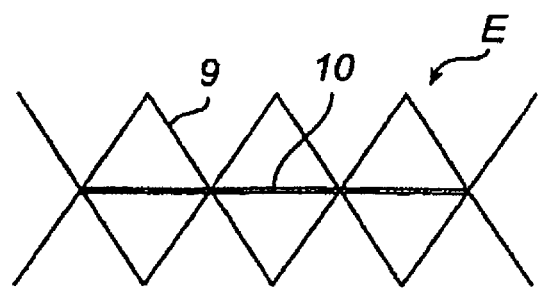
FIGS. 17 and 18 schematically illustrate another device, shown in a first state and a second elongated state, respectively.
Figure 18:
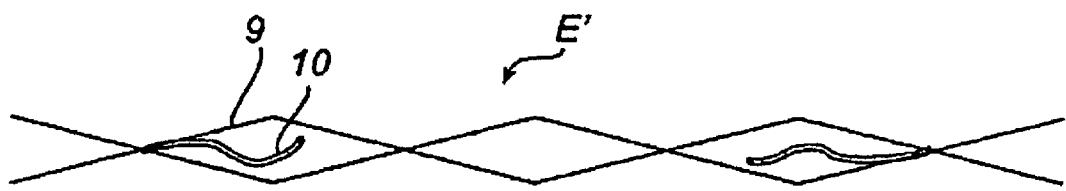

FIG. 17 shows a device according to the basic inventive idea in its non-activated short state of shape E. A scissors-shaped shape-changing member 9 of the device is held in a short state of shape by means of a delay means in the form of a resorbable thread 10, and, thereby, the whole device is held in its short state of shape E. When the delay means 10 is cut off by means of resorption, the shape-changing member 9 will resume its original elongate shape so that the device is transformed to its activated state of shape E' (FIG. 18).

Figure 19:
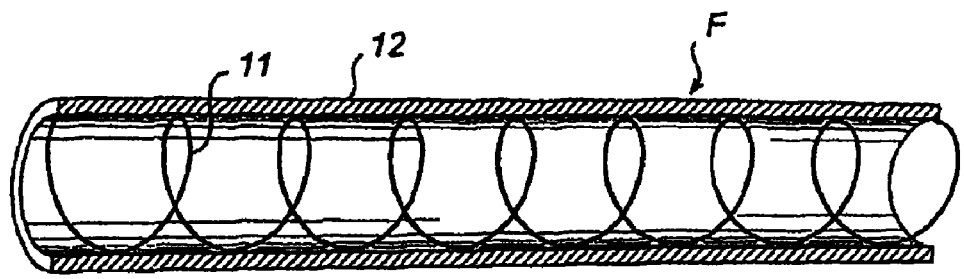
FIG. 19 is a schematic view of yet another device, shown in a first state.
Figure 21:
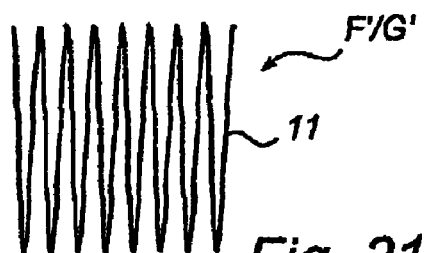

FIG. 19 shows a device according to the basic inventive idea comprising a shape-changing member in the form of a coil 11 of a shape-memory material having been stretched and arranged in a delay means in the form of a tube 12 of resorbable material. The device is then in its non-activated state of shape F. When the delay means 12 has been sufficiently resorbed, the shape-changing member 11 will resume its original shorter and wider shape as shown in FIG. 21, and the device is transformed to its activated state of shape F'.

Figure 20A:
FIG. 20a is a schematic view of another device being an alternative to the device shown in FIG. 19 and being shown in a first state.
Figure 20B:
FIG. 20b is a schematic view of a device according to FIG. 20a, illustrating the structure of a part of the device.

In an alternative device shown in FIGS. 20a and 20b according to the basic inventive idea, the tube 12 in FIG. 19 is replaced by a resorbable rod 13 provided with grooves 13a in which a coil 11 is initially wound. The winding of the coil 11 in the grooves 13a obstructs the coil 11 from resuming its original shape (FIG. 21) and, hence, the device is held in its non-activated state of shape G by the rod 13, as illustrated in FIG. 20a. By resorption of the rod 13 in e.g. a human body, the shape-changing force of the coil 11 is released and the device is transformed to its activated state of shape G' as shown in FIG. 21.

Figure 22:
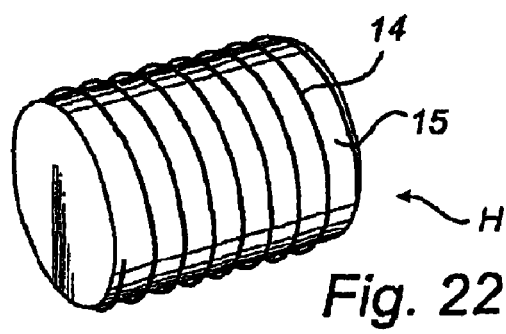
FIGS. 22 and 23 are schematic views illustrating another device, shown in a first state and a second state, respectively.
Figure 23:
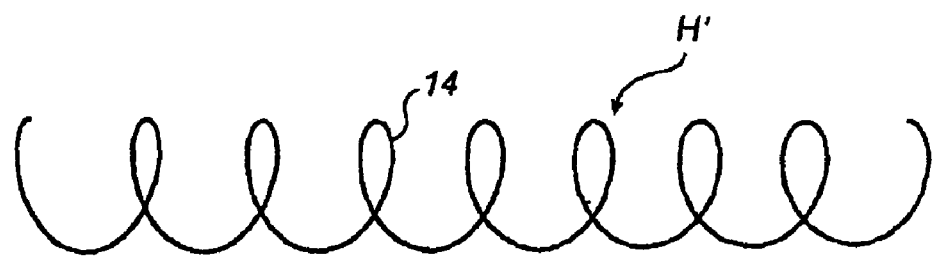

In another device shown in FIG. 22 according to the basic inventive idea, a coil 14 is wound around a resorbable rod 15. When the rod 15 is resorbed, the shape-changing forces of the coil 14 will be released so that the coil 14 resumes an original elongate shape, as shown in FIG. 23, whereby the device is transformed from its non-activated state of shape H to its activated state of shape H'.

Figure 24:
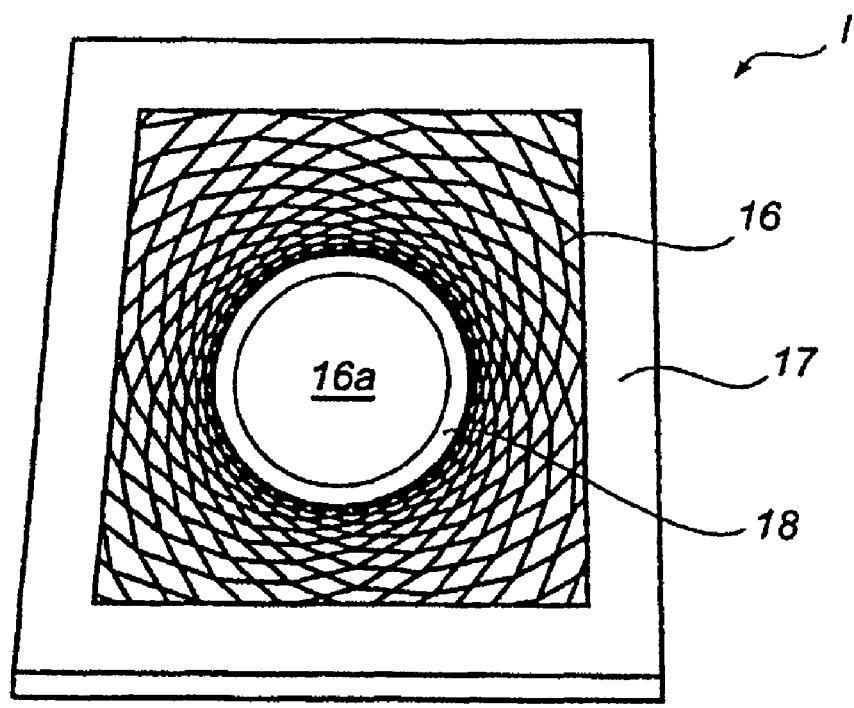
FIG. 24 is a schematic perspective view of a device for two-dimensional contraction.

FIG. 24 shows a device according to the basic inventive idea in the form of a patch for closing or obstructing openings, e.g. in the heart of a human or animal body. The patch has a shape-changing member 16 comprising a grid matrix formed by threads made of memory material such as Nitinol or SMP. The threads may be covered individually by biocompatible material such as PTFE or dacron to fill in the gaps between the threads, e.g. in the way shown in FIG. 26 with threads 28 and biocompatible material 29.

The patch in FIG. 24 further comprises a frame 17 for anchoring the patch in the body, e.g. by means of sutures. The frame may be made of any biocompatible material, such as PTFE or dacron. By the use of a cone (not shown), the threads may be spread apart, creating a central opening 16a in the patch. The cone is advanced until a delay means 18 in the form of a separate ring 18 of a resorbable material, initially positioned on the cone, is positioned in the opening 16a. The cone is then drawn back and the ring 18 is left in the opening 16a, restraining the elastic threads in such a way that the central opening 16a in the patch is maintained. FIG. 24 shows the patch in its non-activated state of shape I with the ring 18 positioned centrally. After implant and sufficient resorption of the restraining ring 18 and after a specified period of time, the central opening in the patch is closed and the patch is activated.

Figure 25:
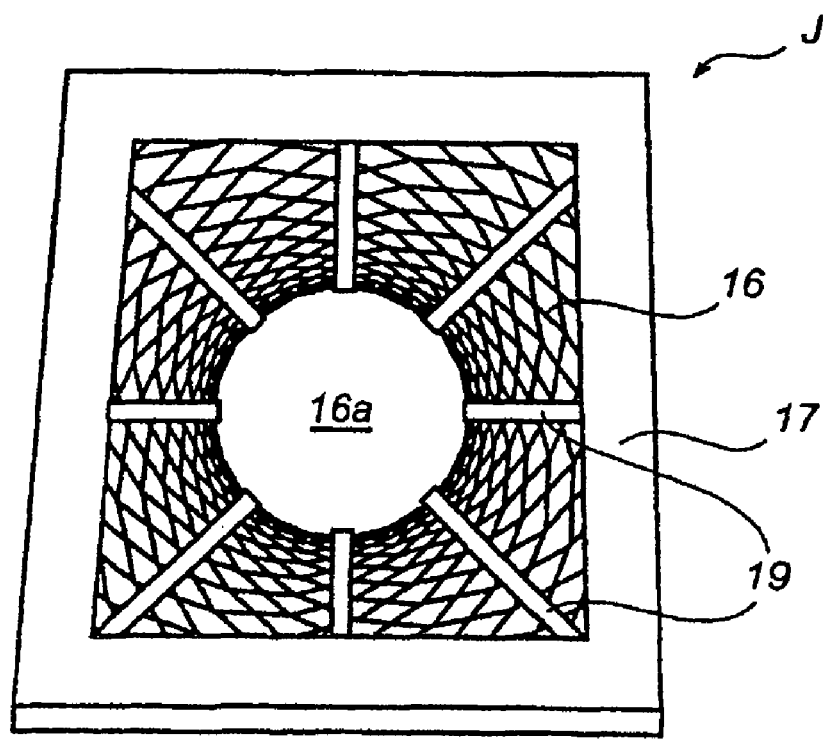
FIG. 25 is a schematic perspective view of another device for two-dimensional contraction.

FIG. 25 shows an alternative device according to the basic inventive idea in the form of a patch for closing openings. The patch may be constructed by attaching delay means 19 in the form of resorbable threads or bands 19 to the top of a sharp cone and down along the sides of the cone, advancing the cone through the middle of the patch so that the elastic threads 16 are spread out and thus an opening 16a in the patch is created, and fastening one end of each band to the frame 17 on one side of the patch and the other end of each band 19 to the frame 17 on the other side of the patch, so that each band 19 encircles the opening. The bands 19 could be placed at regular intervals along the circumference of the opening so that they expand a substantially circular hole in the middle of the patch. By means of the resorbable bands 19, the patch is held in its non-activated state of shape J.

The single shape-changing thread in FIGS. 6 to 14 may be replaced by several threads or by one or more bands. The scissors-shaped members 7 and 9 in FIGS. 15 to 18 may be multiplied so as to form a scissor-shaped area, which in turn may be shaped into different forms. The single tube in FIGS. 8, 12, 15 and 19 may be slotted or may be divided into several tube segments. A delay means may also be provided in the form of resorbable glue, which holds parts of the shape-changing member together and in that way delay the change of shape of the device.

Figure 26:
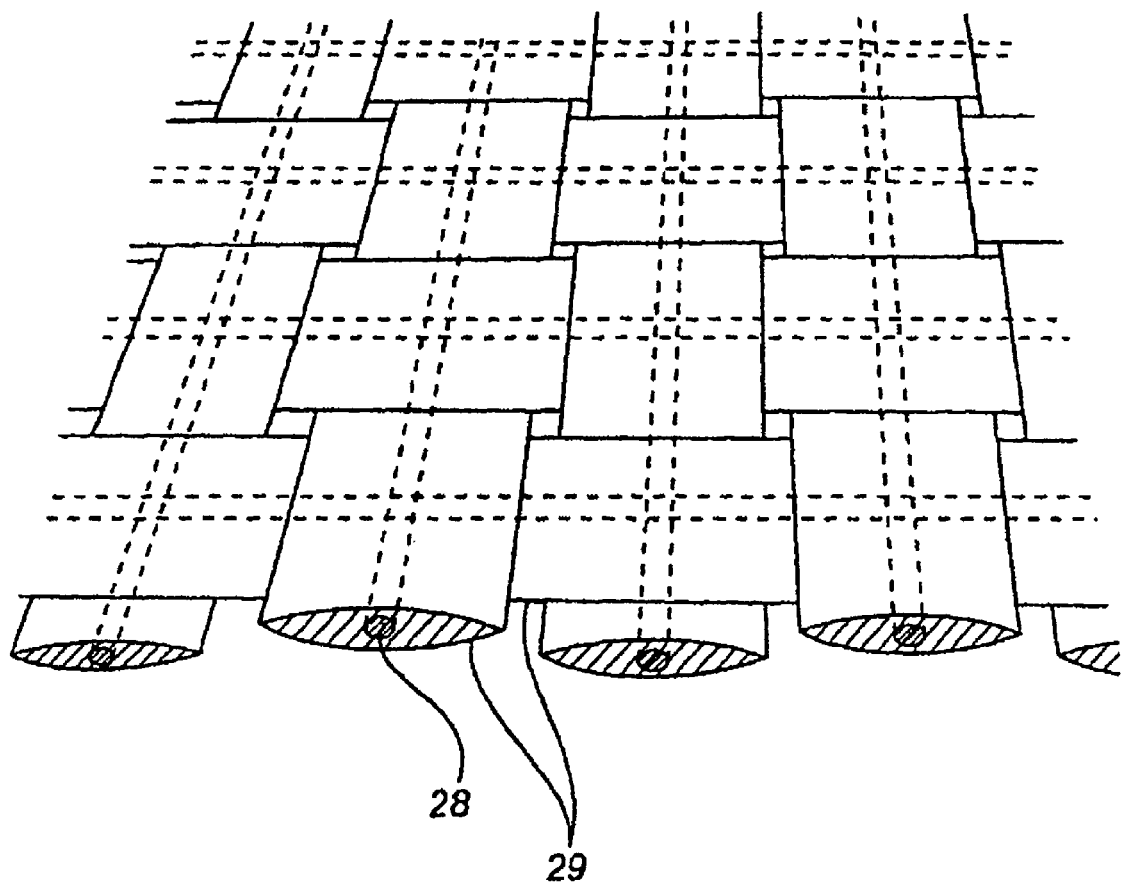
FIG. 26 is a schematic perspective view illustrating a part of one possible arrangement of a device presenting a reshapable area.

FIG. 26 shows one possible arrangement of a part of a contractable area according to the basic inventive idea. The contractable area comprises a shape-changing member in the form of a grid matrix of shape memory metal threads 28 covered by a delay means in the form of a fabric of a resorbable material (it should be noted that FIG. 26 was previously used to illustrate how the threads of the patches of FIGS. 24 and 25 may be covered with biocompatible material). The fabric comprises resorbable bands 29 which have been weaved together to form an area. Each of the resorbable bands 29 is solid except for a cylindrical hollow space in which a thread 28 is located, just like the thread 1 is located inside the tube 2 in FIG. 8.

The bands 29 restrain the threads 28 from being folded to their original curved shapes as long as the fabric 29 is not resorbed.

Analogously to the device in FIG. 8, there may be a radial play between the inner wall of each band 29 and the thread 28 being located inside it, in which play the thread 28 can move without consequently being able to change the size of the area of the device to any larger extent.

Further, the hollow space in each band 29 must not necessarily be cylindrical. In fact, if the width of each band 29 is small enough as compared to the curves that the threads 28 will assume when being "activated" as a result of the bands 29 being resorbed, the bands 29 may be hollow.

The contractable area in FIG. 26 may be manufactured by threading a thread 28 of a memory material into each resorbable band 29 and then weaving the bands 29 with threads 28 together to form the fabric as illustrated in FIG. 26.

Another possible way of making a contractable area according to the basic inventive idea would be to arrange threads or bands of a memory material in a grid matrix and to fix the threads or bands together with resorbable crosslinks. The resorbable crosslinks would then restrain the threads or bands from being folded as long as enough resorbable material in the crosslinks is left unresorbed.

The basic inventive idea opens up for new possibilities within many medical applications.

The basic inventive idea would for example be useful where openings of human, or animal, organs or other structures need to be opened or closed slowly. For instance, when an opening between the left and right side of the heart is present, an immediate closure of the opening could be dangerous, whereas a slower closure would be tolerated.

Within many medical areas, the basic inventive idea would be useful when a continuous long-term effect of shape-changing forces is desired. One such application would be a device designed to shorten or lengthen a human or animal structure in one or more dimensions. The device would then have time to heal into the body structure before shape-changing forces are released and force the body structure to slowly change its shape.

This could for example be useful in the area of orthopaedics for lengthening of a bone structure.

For orthodontic treatment, the basic inventive idea would be useful when it comes to tooth-regulation and lengthening of the maxilla and/or mandibula, i.e. the upper and lower jaws.

In plastic surgery an extra growth of skin area is often used to cover skin defects. Using the basic inventive idea, a slow growth of skin area would be augmented.

An example within the area of urology surgery is lengthening of a penis. In this case a device made of three segments could be designed, where the distal ends of the device first are allowed to grow into the tissue. After fixation of the two ends of the device in the penis tissue, the mid portion which temporarily has been restrained by means of a resorbable material as described above will be released and the mid portion of the device will grow in length. One specific capacity of a human or animal body is to allow slow deformation of organs or tissues by compensatory tissue adaptation. A penis would therefore grow slowly to a predetermined length.

By means of the basic inventive idea, a sequential effect of shape-changing forces could also be provided, i.e. change of shape could occur in two or several steps as a result of resorbable material releasing the shape-changing forces in predetermined steps. In each step, a part or parts of a device could first heal into a body structure and secondly the desired shape-changing effects could be released.

As seen from the examples above, a substantial advantage of the basic inventive idea is that a change of shape is allowed to be made slowly so that body tissues have time to adapt.

Another medical application of particular interest, which could be improved by using the basic inventive idea, is treatment of pathological alveolar sac growth. Some background of this disease will be given next.

Chronic obstructive pulmonary disease (COPD) is an umbrella term used to describe airflow obstruction that is associated mainly with emphysema and chronic bronchitis. COPD is the fourth leading cause of death in the U.S. in 1998, according to the National Center for Health Statistics, Report of Final Morbidity Statistics, 1998. Emphysema causes irreversible lung damage by weakening and breaking the air sacs within the lungs. Further, sick air sacs sometimes grow unrestrainedly and repress smaller air sacs, resulting in lack of oxygen and by time death. This disease is hard to treat. At present, surgical treatment of dilated air sacs involves cutting them away, but this treatment gives no long-term effect since a new air sac will soon start to grow.

This known method for treatment of alveolar sac growth requires, whether it is effective or not, major lung surgery which, as mentioned before, is particularly hazardous to certain groups of patients. Therefore a less invasive method for treatment of alveolar sac growth is desired.

A contractable area, as the one shown in FIG. 26, may be formed into a contractable sheet for treatment of alveolar sac growth, e.g. emphysematic pulmonary diseases.

Figure 27:
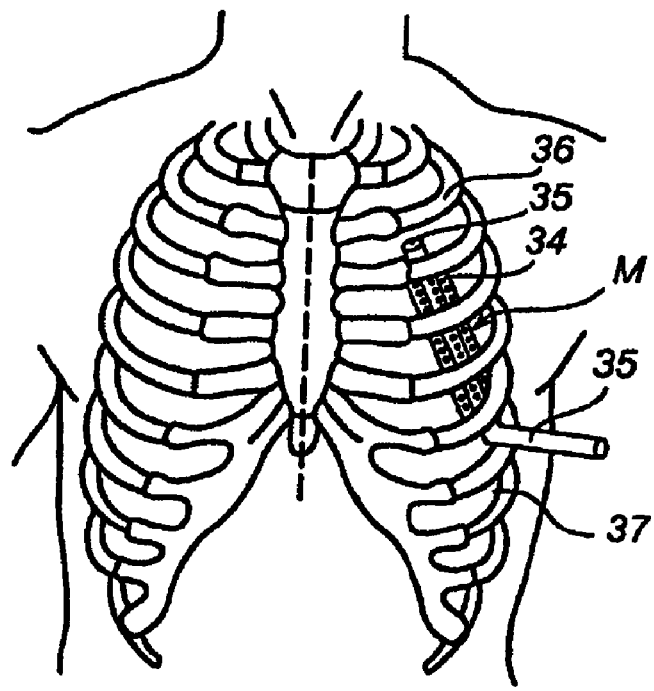
FIGS. 27 and 28 are schematic views illustrating the positioning of an embodiment of a device for treatment of chronic obstructive pulmonary disease.
Figure 28:
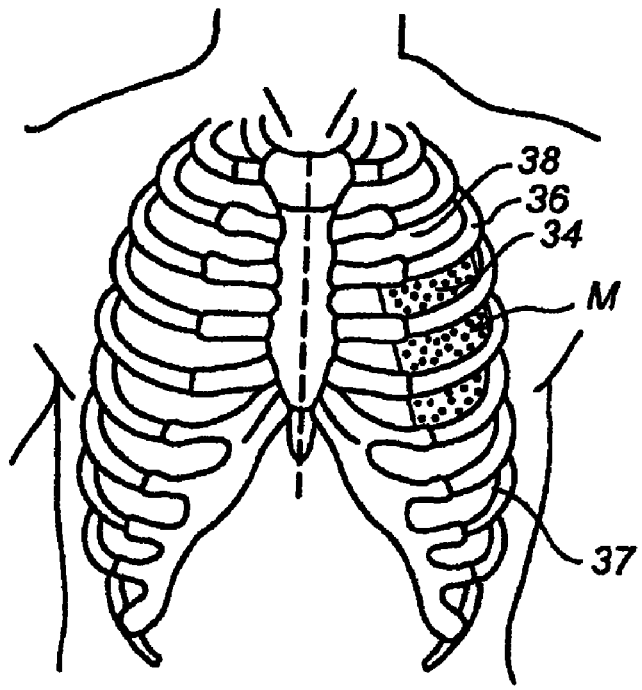

FIGS. 27 and 28 show the use of a device according to the basic inventive idea for treatment of alveolar sac growth.

Referring to FIG. 27, a contractable sheet 34 in its non-activated state of shape M is rolled up on a catheter 35, introduced between ribs 36 into the pleural cavity (the space between the pleura of the lung and the pleura of the chest wall), and placed upon the lung 38 surface to be treated.

The contractable sheet 34 may also be inserted into the body by means of open surgery or by means of endoscopic surgery and positioned on an organ surface.

Now referring to FIG. 28, the sheet 34 is then rolled out over the lung 38 and the catheter 35 is removed.

The sheet 34 is arranged to grow fixed to the lung surface so that subsequent contraction of the sheet 34, as a result of the resorbable material of the sheet 34 being resorbed, causes the sheet 34 to compress the lung 38 by means of a force of the shape memory metal threads in the sheet 34. Hence, bullae and areas of enlarged alveolar sacs may be shrunk or eliminated and further pathological growth of alveolar sacs may be prevented.

In this case the contractable sheet 34 contracts in two directions, one approximately vertical and one approximately horizontal. The sheet 34 could also be designed to contract in one direction only, e.g. the most horizontal one, or contract in a circular mode, and still be able to shrink bullous areas and prevent alveolar sacs from growing.

According to the basic inventive idea, a device for treatment of pathological lung growth is implantable into the body of an organism and comprises an elastic contractable member being arranged to enclose at least part of the lung of the organism, and a delay means being arranged to delay contraction of the contractable member when the device is implanted in the body of the organism by counteracting the contraction during resorption of the delay means by the surrounding body of the organism.

A basic advantage of this device is that the device, since said contractable member is elastic, can be inserted into the body using catheter-guided techniques. Hence, less invasive treatments can be provided.

Another advantage, which comes both from the elasticity and the delayed contraction, is that the device can be inserted by means of catheter-guided techniques even if said contractable member comprises a large area. This is due to the fact that the substantially elastic device at the insertion can be rolled up on a catheter and then be unfolded to enclose said organ.

After a period of time after the surgical or percutaneous insertion, the device will start to contract as a result of the delay means being resorbed. The contraction will then make the device enclose the organ tight and apply a restraining force which holds back the growth of the organ. Since the implanted device applies a continuous restraining force to the organ, more long-term effects can be achieved in treatment of growing body organs. It is to be noted that if the contraction of the device would not have been delayed, it would have been very difficult to roll up the device on a catheter and then unfold it round the organ.

Preferably, said contractable member comprises a shape memory material, e.g. Nitinol.

A method for treatment of pathological lung growth according to the basic inventive idea comprises the steps of inserting a restraining device into the body of an organism, enclosing the lung of the organism with the restraining device, compressing said restraining device by means of a contractable member of said restraining device, and delaying said compression by a resorbable delay means.

The method may be used for treatment of bullous emphysema. It may also be used for treatment of alveolar sac growth.

A device according to the basic inventive idea may be fixed in body tissue by other means in combination with or instead of the healing process allowed by the delaying of the change of shape. Hence, fixing of a device according to the basic inventive idea may as well be accomplished for example by means of suturing, gluing, clipping or using hooks. These means of fixation would permit a better healing in of the device in the tissue and also prohibit dislocation while healing in.

As already seen, the number of advantages of a device according to the basic inventive idea is large, of which a few are mentioned next. The basic inventive idea provides:
1. less invasive surgical treatments;
2. devices that are properly fixed inside the body by means of parts healing into the body tissue;
3. devices to be designed that have multiple purposes;
4. eliminating stabilizing surgical instruments for keeping a present shape of the device during operation;
5. engineering to decide when a shape-changing action by the device is to take place in the body;
6. a change of shape to be made slowly so that body tissue has time to adapt.

Figure 29:
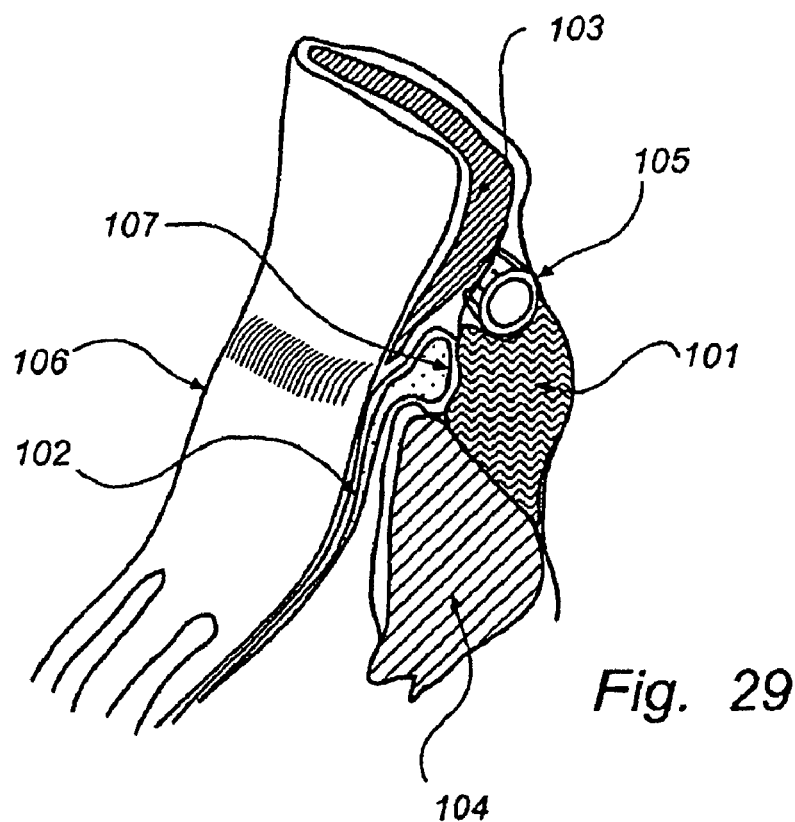
FIG. 29 is a cross-sectional view of a part of a heart.

FIG. 29 is a cross-sectional view through the heart area of posterior atrioventricular groove 101, which is filled with fatty tissue. It shows posterior leaflet 102 of the mitral valve and adjoining parts 103, 104 of the atrial myocardium and the ventricular myocardium. Coronary sinus 105 is shown close to mitral annulus 106 and behind attachment 107 of posterior leaflet 102. Since coronary sinus 105 substantially encircles mitral annulus 106, a reduction of the radius of curvature of bent coronary sinus 105 also will result in a diameter and circumference reduction of mitral annulus 6.

In an adult, the course of coronary sinus 105 may approach within 5-15 mm of the medial attachment of posterior leaflet 102 of the mitral valve. Preliminary measurements performed at autopsies of adults of normal weight show similar results, with a distance of 5.3+/−0.6 mm at the medial attachment and about 10 mm at the lateral aspect of posterior leaflet 102. The circumference of coronary sinus 105 was 18.3+/−2.9 mm at its ostium (giving a sinus diameter of the septal aspect of the posterior leaflet of 5.8+/−0.9 mm) and 9.7+/−0.6 mm along the lateral aspect of posterior leaflet 102 (corresponding to a sinus diameter of 3.1+/−0.2 mm).

In accordance with the principles of the present invention, devices and methods for treating mitral insufficiency are provided, wherein the circumference of the mitral valve annulus is reduced when the device is deployed and/or actuated in at least a portion of the coronary sinus.

Devices constructed in accordance with principles of the present invention may comprise one or more components suitable for deployment in the coronary sinus and adjoining coronary veins. The device may be configured to bend in-situ to apply a compressive load to the mitral valve annulus with or without a length change, or may include multiple components that are drawn or contracted towards one another to reduce the circumference of the mitral valve annulus. Any of a number of types of anchors may be used to engage the surrounding vein and tissue, including hooks, barbs, flanges, partial or completely through-wall tee structures, or biological anchoring. Where multiple components are provided, reduction of the mitral valve annulus may be accomplished during initial deployment of the device, or by biological actuation during subsequent in-dwelling of the device.

Figure 30:
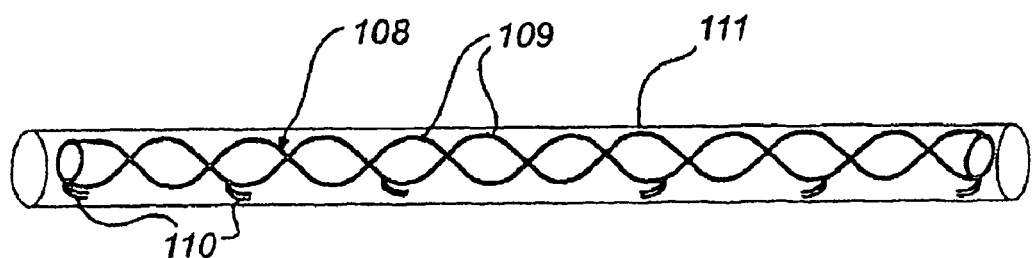
FIGS. 30-31 are schematic views of a first embodiment according to the present invention.
Figure 31:
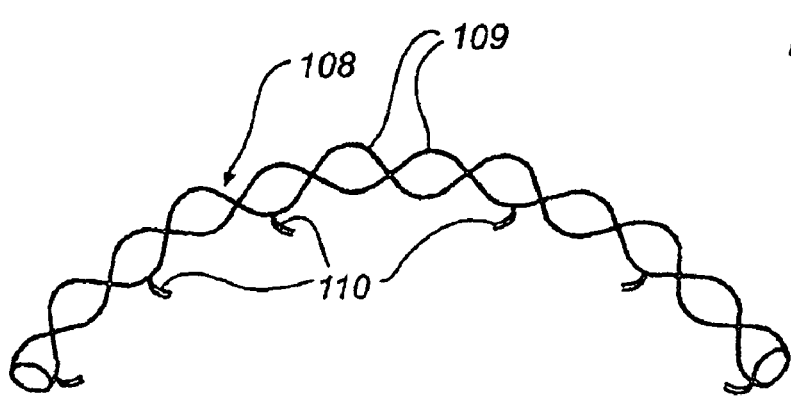

With respect to FIGS. 30 and 31, a device that experiences shortening during deployment is described as comprising an elongate body 108 made of memory metal, e.g. Nitinol, or other similar material which has a memory of an original shape, illustrated in FIG. 31, and which can be temporarily forced into another shape, illustrated in FIG. 30. Elongate body 108 comprises one, two or more memory metal strings 109 of helical or other shape so as to fit together and be able of to permit the movements described below. Along elongate body 108, plurality of hooks 110 are fastened so as to extend radially out therefrom. Hooks 110 are covered by a cover sheath 111 in FIG. 30.

Figure 32:
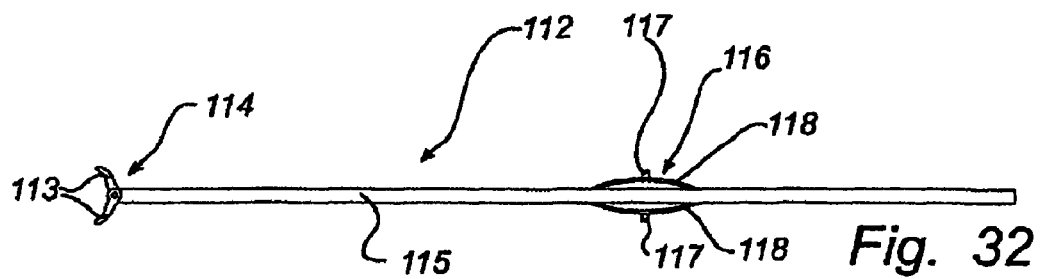
FIGS. 32-34 are schematic views illustrating an instrument that may be used when positioning the device of FIGS. 30-31 in the coronary sinus.

Elongate body 108 is forced into a stretched or extended state by means of stabilizing instrument 112 shown in FIG. 32. Instrument 112 has two arms 113 at distal end 114 of rod 115 and locking means 116 at proximal end of rod 115. The distance between the ends of rod 115 corresponds to the desired length of elongate body 108 when being inserted into coronary sinus 105.

Figure 33:
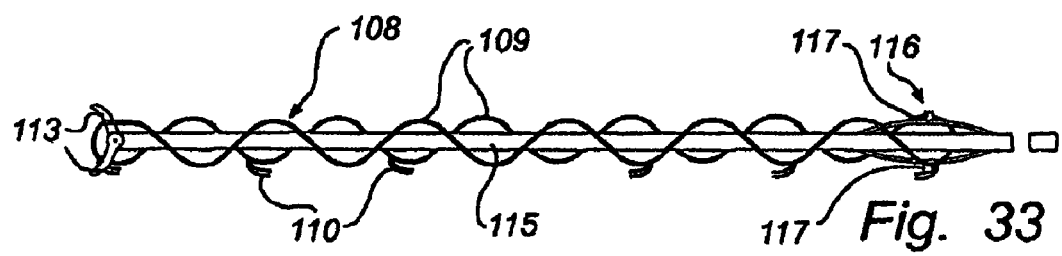
Figure 34:
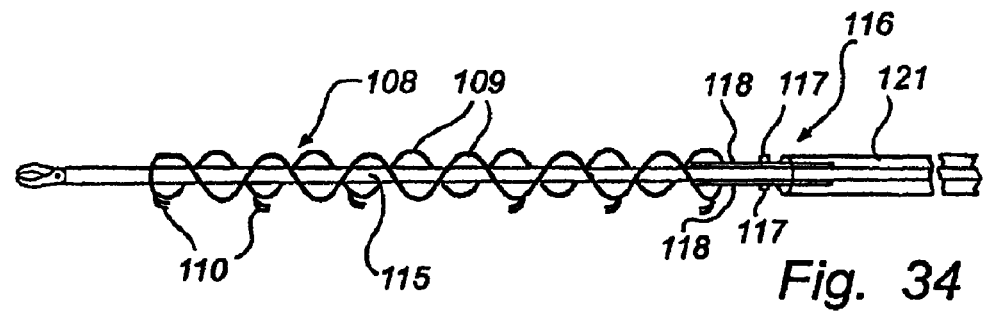

Arms 113 are free to move between the position shown in FIG. 32 and a position in alignment with rod 115, as shown in FIG. 34. Locking means 116 has two locking knobs 117, which are pressed radially outwards from rod 115 by two spring blades 118. Thus, elongated body 108 can be pushed over rod 115 of stabilizing instrument 112, then stretched between arms 113 and knobs 117, and finally locked in its stretched state on stabilizing instrument 112 between arms 113 and knobs 117, as illustrated in FIG. 33.

Rod 115 may be a metal wire which is relatively stiff between distal end 114 and locking means 116 but still so bendable that it will follow the shape of coronary sinus 105. Proximally of locking means 116 the metal wire of stabilizing instrument 111 is more pliable to be able to easily follow the bends of the veins.

The above-described elongate body 108 is positioned in the coronary sinus 105 in the following way:

An introduction sheath (not shown) of synthetic material may be used to get access to the venous system. Having reached access to the venous system, a long guiding wire (not shown) of metal is advanced through the introduction sheath and via the venous system to coronary sinus 105. This guiding wire is provided with X-ray distance markers so that the position of the guiding wire in coronary sinus 105 may be monitored.

Figure 36:
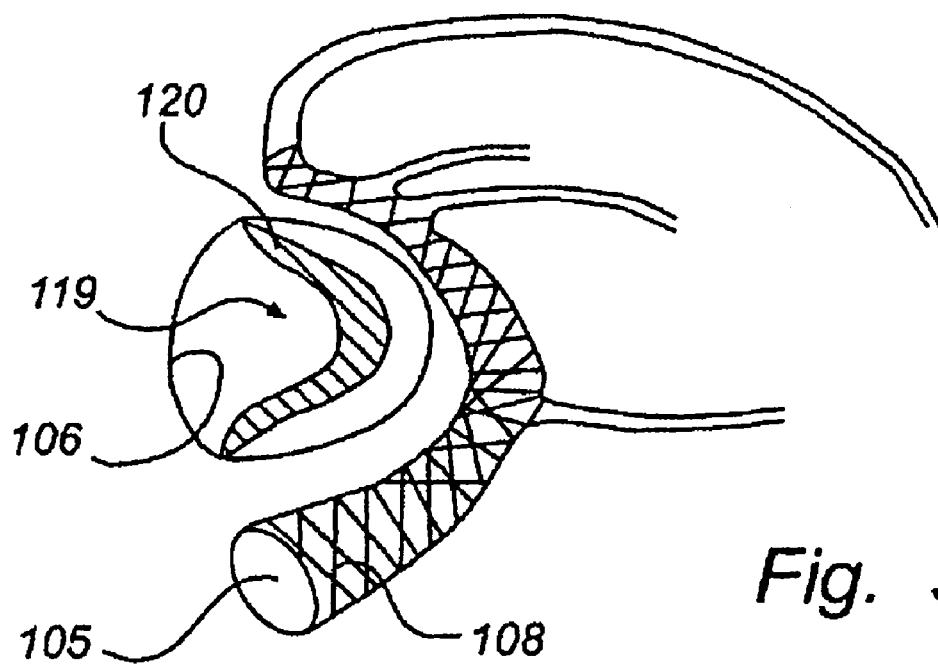
FIGS. 36-37 are schematic views illustrating the positioning of the device of FIGS. 30-31 in the coronary sinus.

Elongate body 108 is locked onto stabilizing instrument 112, as shown in FIG. 33, and introduced into long cover sheath 111 of synthetic material. This aggregate is then pushed through the introduction sheath and the venous system to coronary sinus 105 riding on the guiding wire. After exact positioning of elongate body 108 in coronary sinus 105, as illustrated in FIG. 36 where mitral valve 119 is shown having central gap 120, cover sheath 111 is retracted to expose elongate body 108 within coronary sinus 105. This maneuver allows hooks 110 on elongate body 108 to dig into the walls of coronary sinus 105 and into the heart. Elongate body 108 is still locked on to stabilizing instrument 112 such that hooks 110 engage the walls of coronary sinus 105 in the stretched or extended state of elongate body 108.

Figure 37:
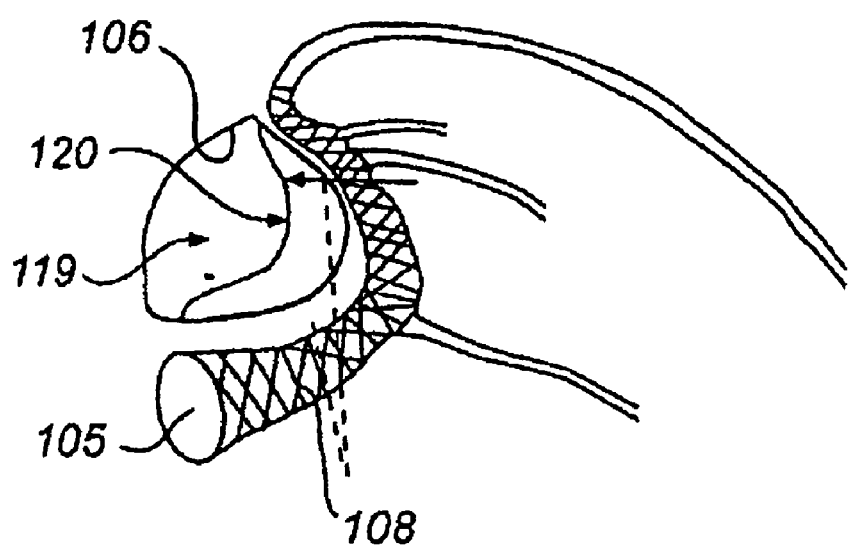

Catheter 112, shown in FIG. 34, is pushed forward on the guiding wire and rod 115, to release elongate body 108 from locking means 116 by pressing spring blades 118 toward rod 115. This movement releases knobs 117 as well as arms 113 from engagement with elongate body 108, which contracts elongate body 108 as illustrated in FIG. 37, thereby shortening the radius of curvature of coronary sinus 105. As a result, mitral valve annulus 106 shrinks moving the posterior part thereof forward (shown by arrows in FIG. 37). This movement reduces the circumference of mitral valve annulus 106 and thereby closes central gap 120.

Figure 35:
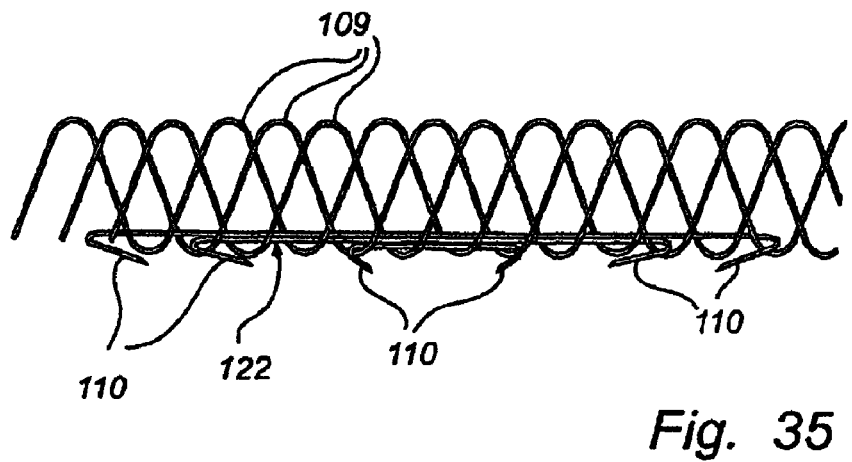
FIG. 35 is a partial, enlarged view of the first embodiment shown in FIG. 30.

FIG. 35 illustrates a part of an arrangement of wires 109 and hooks 110 along a peripheral part of elongate body 108, whereby elongate body 108 will be asymmetrically contracted resulting in a bending thereof when interconnecting parts 113 of at least some of hooks 110 are shortened to an original shape.

Figure 38:
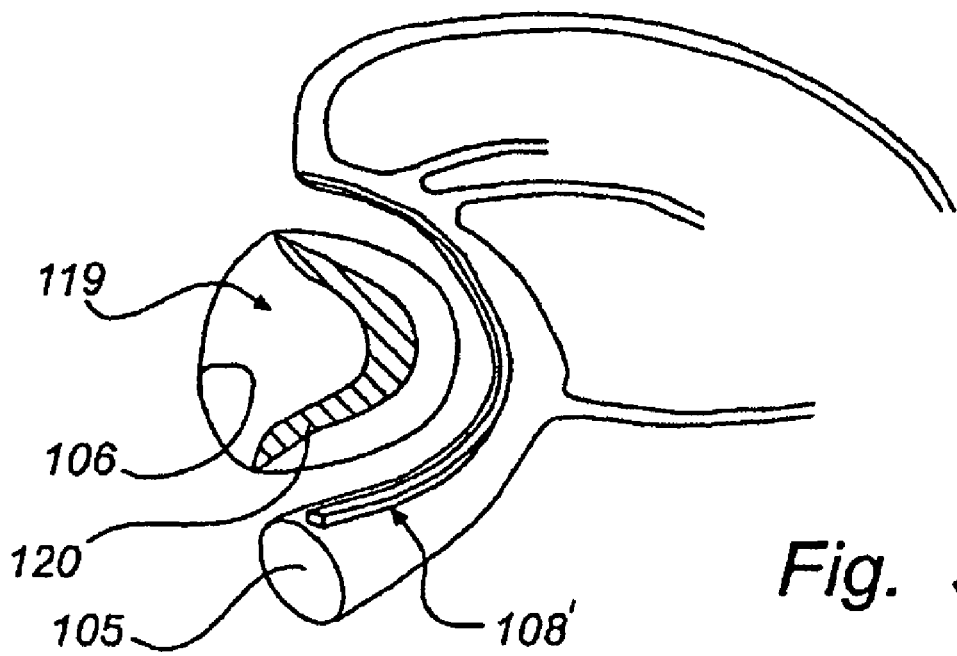
FIGS. 38-39 are schematic views illustrating the positioning of a solid U-shaped wire within the coronary sinus.
Figure 39:
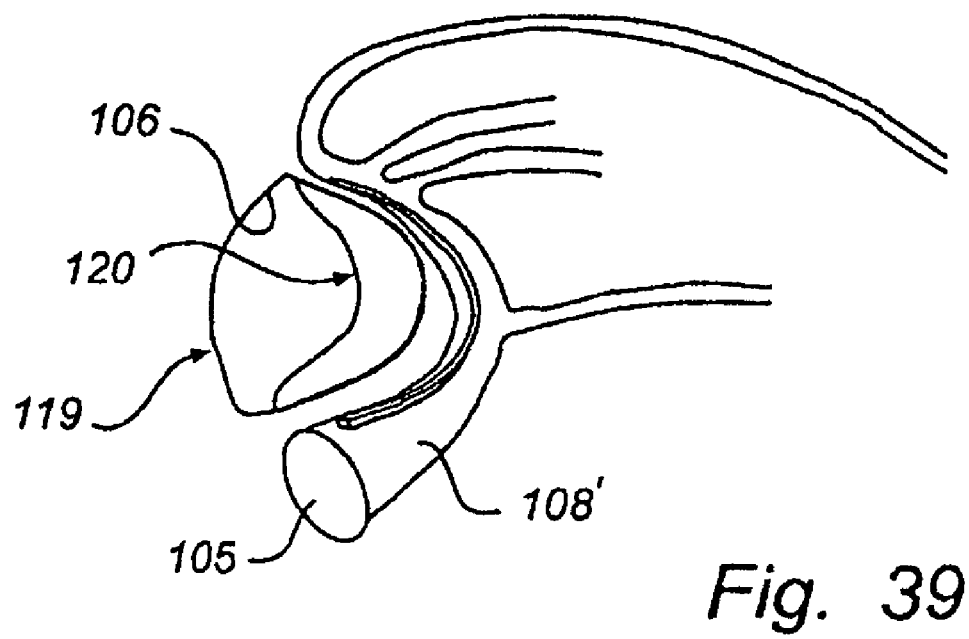

FIGS. 38 and 39 illustrate an alternative embodiment of an elongate body 108' which does not experience shortening during deployment. Elongate body 108' comprises a solid wire in the shape of an open U-shaped ring that will engage the wall of coronary sinus 105 most adjacent to mitral valve annulus 106 when inserted into coronary sinus 105. Elongate body 108' consists of a memory metal material which when reverting to its original shape will bend as illustrated in FIG. 39. The return of open ring 108' to its original shape may be initiated in several ways, as is obvious to the man skilled in the art.

Further embodiments comprising two or more stent sections that are coupled by a system of wires and eyelets are described in co-pending U.S. patent application Ser. No. 09/775,677, filed Feb. 5, 2001, which is incorporated herein by reference. In the embodiments described therein, individual proximal and distal stents are first deployed in the coronary sinus, and a cinch mechanism, illustratively comprising a wire and eyelets, is used to draw the proximal and distal stent sections towards one another, thereby reducing the circumference of the mitral valve annulus.

Referring now to FIGS. 40A-40D, a further alternative embodiment is described, wherein the proximal stent section includes a flange that can be deployed to abut against the coronary ostium. Apparatus 156 comprises device 158 disposed within delivery sheath 160. Device 158 comprises proximal stent section 162 joined to distal stent section 164 via wire 166 and cinch mechanism 167. Proximal and distal stent sections 162 and 164 illustratively are self-expanding stents, but alternatively may comprise balloon expandable stents, coiled-sheet stents, or other type of stent.

Figure 40A:
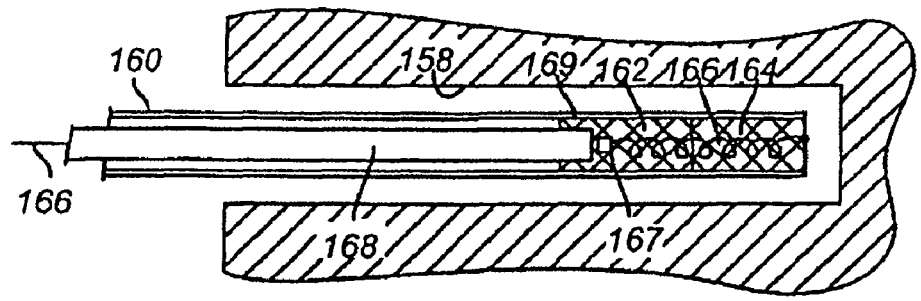
FIGS. 40A-40D illustrate an alternative embodiment comprising a deployable flange coupled to the proximal stent section.

Stents 162 and 164 are disposed within delivery sheath 160 with a distal end of push tube 168 contacting the proximal end of proximal stent section 162. Proximal stent section 162 comprises deployable flange 169. Deployable flange 169 is initially constrained within delivery sheath 160, as shown in FIG. 40A, and preferably comprises a shape memory material, e.g., Nitinol, so that flange 169 self-deploys to a predetermined shape upon retraction of delivery sheath 160.

Wire 166 and cinch mechanism 167 may comprise a combination of wires and eyelets as described in accordance with any of the embodiments in the above-incorporated reference, or any other arrangement that permits the wire to be tightened and locked into position, as will be apparent to one of ordinary skill. Wire 166 includes a proximal portion that remains outside of the patient's vessel for manipulation by a physician, and is configured to reduce the distance between proximal and distal stent sections 162 and 164.

Figure 40B:
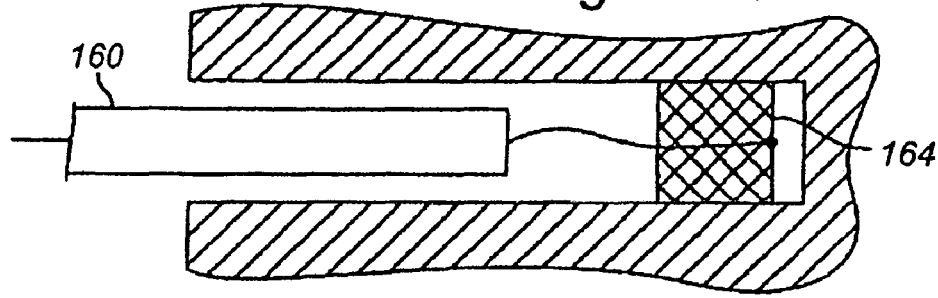

Apparatus 156 is navigated through the patient's vasculature with stents 162 and 164 in the contracted state and into coronary sinus C. The distal end of sheath 160 is disposed, under fluoroscopic guidance, at a suitable position within the coronary sinus, great cardiac vein, or adjacent vein. Push tube 168 is then urged distally to eject distal stent section 164 from within delivery sheath 160, thereby permitting distal stent section 164 to self-expand into engagement with the vessel wall, as shown in FIG. 40B.

Figure 40C:
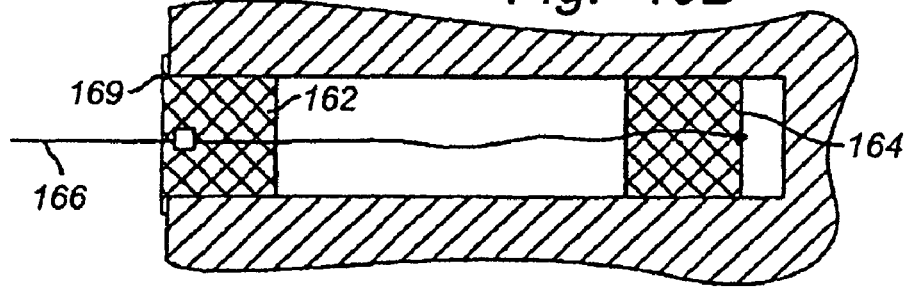

Delivery sheath 160 is then withdrawn proximally, under fluoroscopic guidance, until proximal stent 162 is situated extending from the coronary sinus. Push tube 168 is then held stationary while sheath 160 is further retracted, thus releasing proximal stent section 162. Once released from delivery sheath 160, proximal stent section 162 expands into engagement with the wall of the coronary sinus, and flange 169 abuts against the coronary ostium O, as shown in FIG. 40C.

Figure 40D:
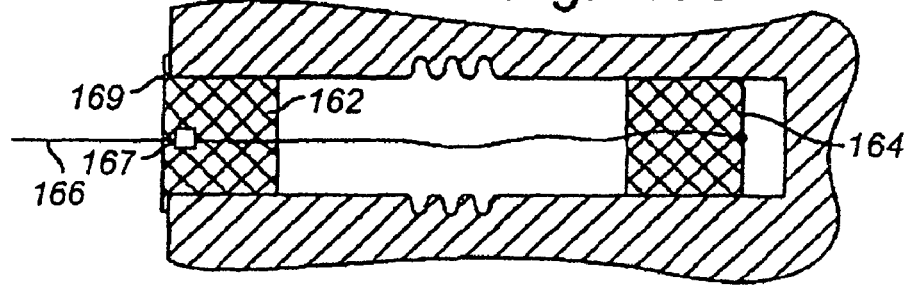

Delivery sheath 160 (and or push tube 168) may then be positioned against flange 169 of proximal stent section 162, and wire 166 retracted in the proximal direction to draw distal stent section 164 towards proximal stent section 162. As will of course be understood, distal stent section 164 is drawn towards proximal stent section 162 under fluoroscopic or other type of guidance, so that the degree of reduction in the mitral valve annulus may be assessed. As wire 166 is drawn proximally, cinch mechanism 168 prevents distal slipping of the wire. For example, wire 166 may include a series of grooves along its length that are successively captured in a V-shaped groove, a pall and ratchet mechanism, or other well-known mechanism that permits one-way motion. Catheter 160 and push tube 168 then may be removed, as shown in FIG. 40D.

Flange 161 may comprise a substantially circular shape-memory member, as illustrated, a plurality of wire members, e.g., manufactured using Nitinol, that self-deploy upon removal of sheath 164 and abut ostium O when proximally retracted, or other suitable shape.

Figure 41A:
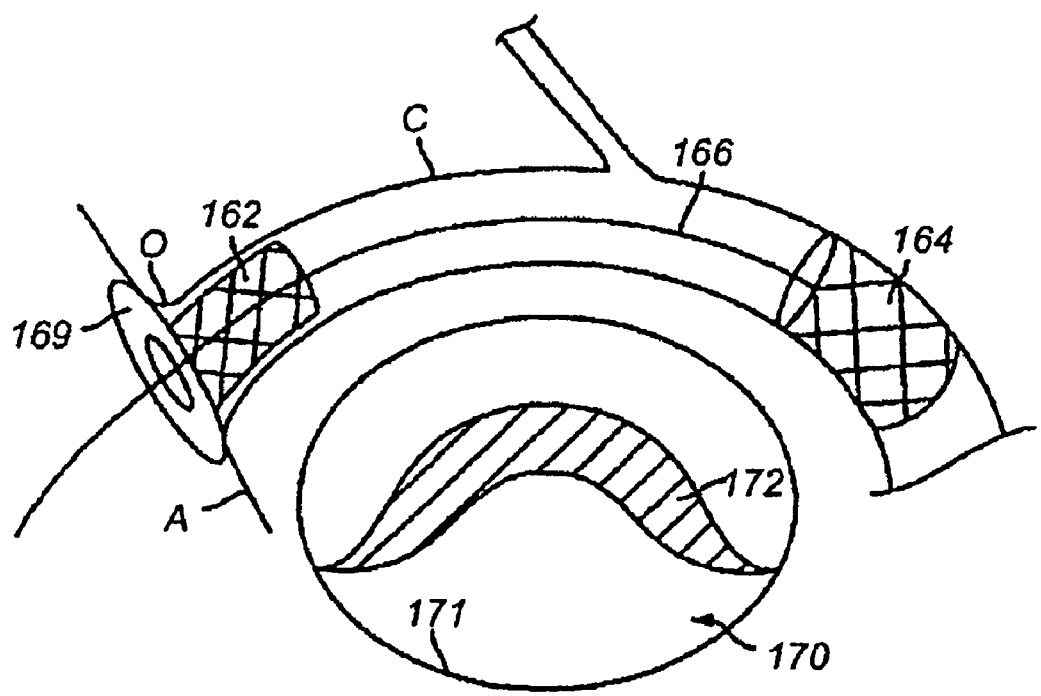
FIGS. 41A-41B illustrate deployment and actuation of the device of FIGS. 40A-40D.
Figure 41B:
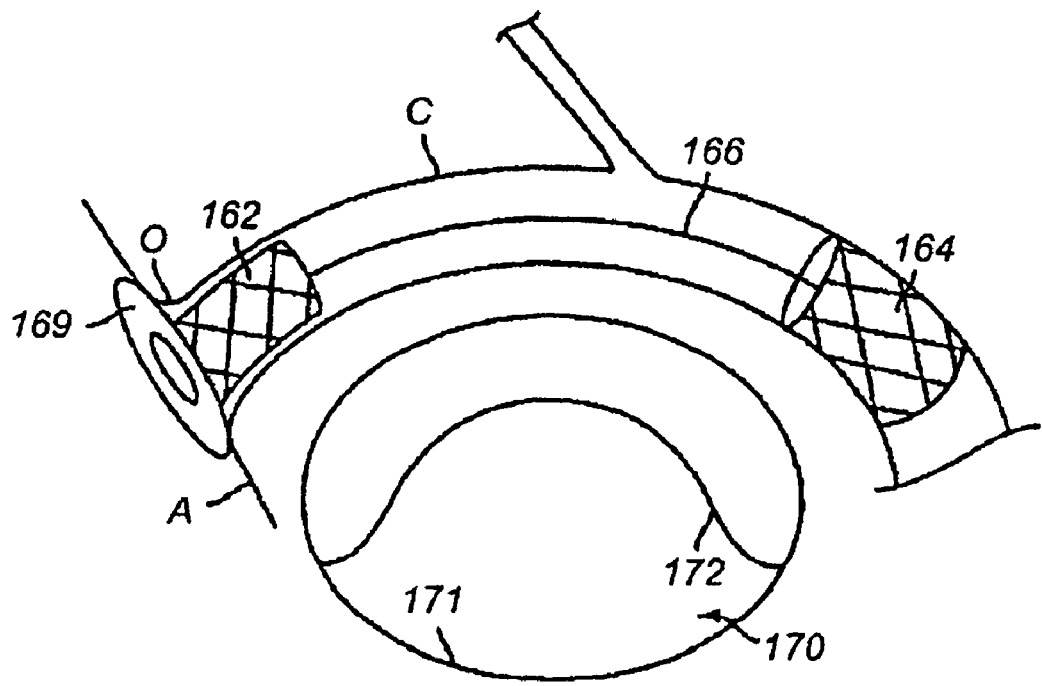

Referring to FIGS. 41A-41B, a preferred method for using apparatus 156 of FIGS. 40A-40D to close a central gap 172 of mitral valve 170 is described. In FIG. 41A, proximal and distal stent sections 162 and 164 are deployed in the coronary sinus so that flange 169 of proximal stent section 162 engages coronary ostium O. Distal stent section 164 is disposed at such a distance apart from proximal stent section 162 that the two stent sections apply a compressive force upon mitral valve 170 when wire 166 and cinch 167 are actuated.

In FIG. 41B, cinch 167 is actuated from the proximal end to reduce the distance between proximal and distal stent section 162 and 164, e.g., as described hereinabove. When wire 166 and cinch mechanism 167 are actuated, distal stent section 164 is pulled in a proximal direction and proximal stent section 162 is pulled in a distal direction until flange 169 abuts coronary ostium O. The reduction in distance between proximal and distal stent sections 162 and 164 reduces the circumference of mitral valve annulus 171 and thereby closes gap 172. Flange 169 provides a secure anchor point that prevents further distally-directed movement of proximal stent section 162, and reduces shear stresses applied to the proximal portion of the coronary sinus.

Figure 42A:
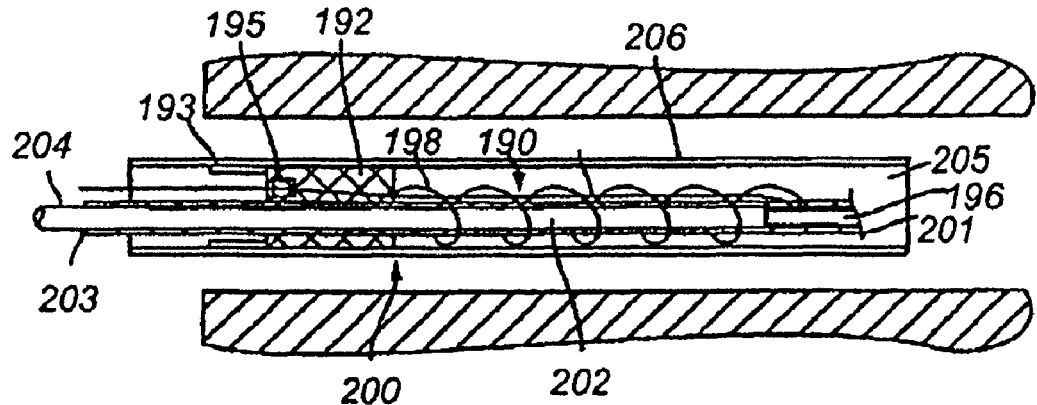
FIGS. 42A-42C illustrate an alternative embodiment of the device of the present invention having a distal anchor.
Figure 42B:
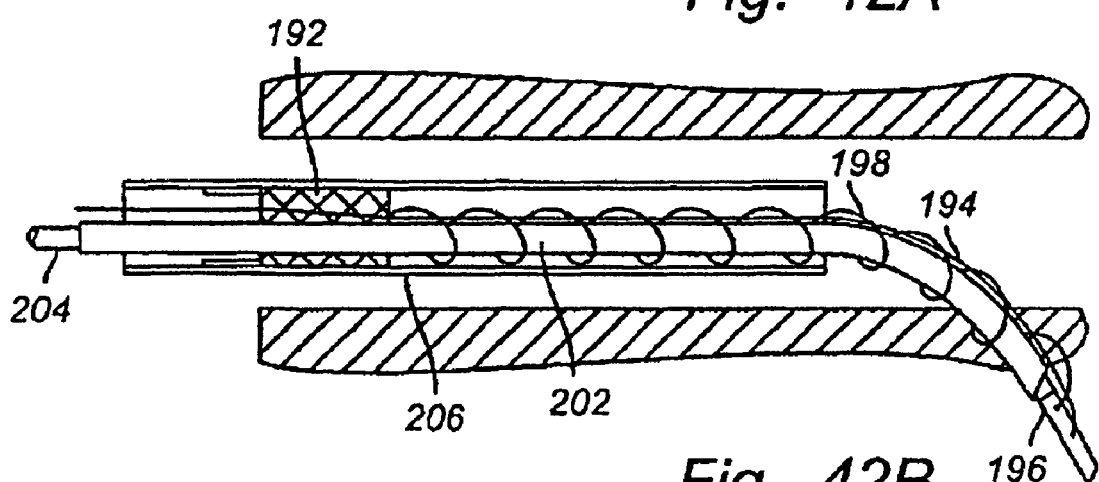
Figure 42C:
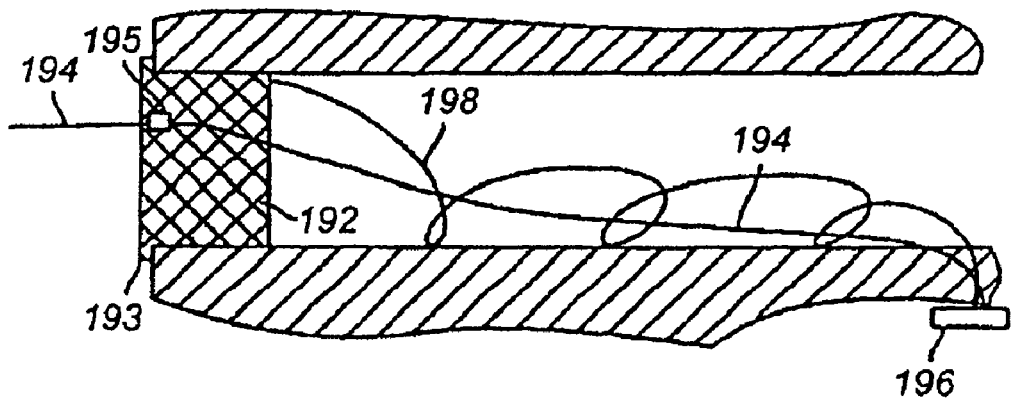

Referring now to FIGS. 42A-42C, a further aspect of the present invention is described, in which the distal stent section of the embodiment of FIGS. 40A-40D is replaced with an anchor that is disposed within or through the myocardium. As will be appreciated, this feature of the device of the present invention may be used either separately or in conjunction with the flange feature described hereinabove. Device 190 comprises proximal stent section 192 coupled by wire 194 and cinch mechanism 195 to distal anchor 196. Proximal stent section 192 may include flange 193. Optional coil section 198 extends distally from proximal stent section 192 to distal anchor 196, and serves to distribute compressive forces created by wire 194 to a larger area of the venous vessel wall.

Device 190 is loaded into delivery apparatus 200 comprising curved stylet 202, push wire 204 and delivery sheath 206. Curved stylet 202 preferably comprises a shape memory alloy capable of being straightened, but adopting a curved shape when extended beyond a distal end of delivery sheath 206. Curved stylet 202 includes sharpened distal tip 201 capable of piercing the left ventricular myocardium, and is disposed in lumen 205 of delivery sheath. Push wire 204 is slidably disposed in lumen 203 of curved stylet 202, and may be advanced distally to eject distal anchor 196 into the left ventricular myocardium or the left ventricle.

As depicted in FIG. 42A, distal anchor comprises a Tee-shaped bar to which wire 194 is coupled. Optional coil section 198 also may be coupled to distal anchor 196, and is contracted around curved stylet 202 when device 190 is loaded into delivery sheath 206. Distal anchor 196 is disposed within lumen 203 of curved stylet so that wire 194 and coil section 198 exit through lateral slot 207 in the stylet. Push wire 204 is disposed in lumen 203 of stylet 202 abutting against the proximal face of distal anchor 196.

In FIG. 42A, device 190 is shown loaded into delivery apparatus 200. Delivery apparatus 200 has been disposed in the coronary sinus using conventional guidance and visualization techniques. The distal end of delivery apparatus 200 is advanced into the coronary venous vasculature to a desired location, and then stylet 202 is advanced distally beyond the end of delivery sheath 206, thereby causing the stylet to regain its curved shape. Further advancement of stylet 202 causes the distal end of the stylet to pierce the coronary vein and extend into the left ventricular myocardium. Push rod 204 is then advanced distally to eject distal anchor 196 into the myocardium, or within the left ventricle, as shown in FIG. 42B.

Stylet 202 and push wire 204 are then withdrawn, and delivery sheath 206 is retracted until the proximal stent section is disposed extending out of the coronary ostium. By selection of the length of wire 194 fed through cinch mechanism 195, proximal stent section 192 may be deployed simply by retracting delivery sheath 206, because distal anchor 196 and wire 194 will prevent further proximal movement of proximal stent section 192. In any event, when proximal stent section 192 is released from delivery sheath 206, it self-expands to engage the vessel wall while flange 193 contacts the coronary ostium, as shown in FIG. 42C.

The proximal end of proximal wire 194 extends through lumen 205 of delivery sheath 206 and may be manipulated by a physician. As in the previous embodiment, once the proximal stent section is deployed, wire 194 may be pulled proximally, with cinch mechanism 195 taking up any slack. The distance between distal anchor 196 and proximal stent section 192 may therefore be reduced a desired amount, causing a corresponding reduction in the circumference of the mitral valve annulus. Optional coil section 198, if present, assists in redistributing the compressive forces applied by wire 194 to the interior surface of the venous vessel.

Figure 43A:
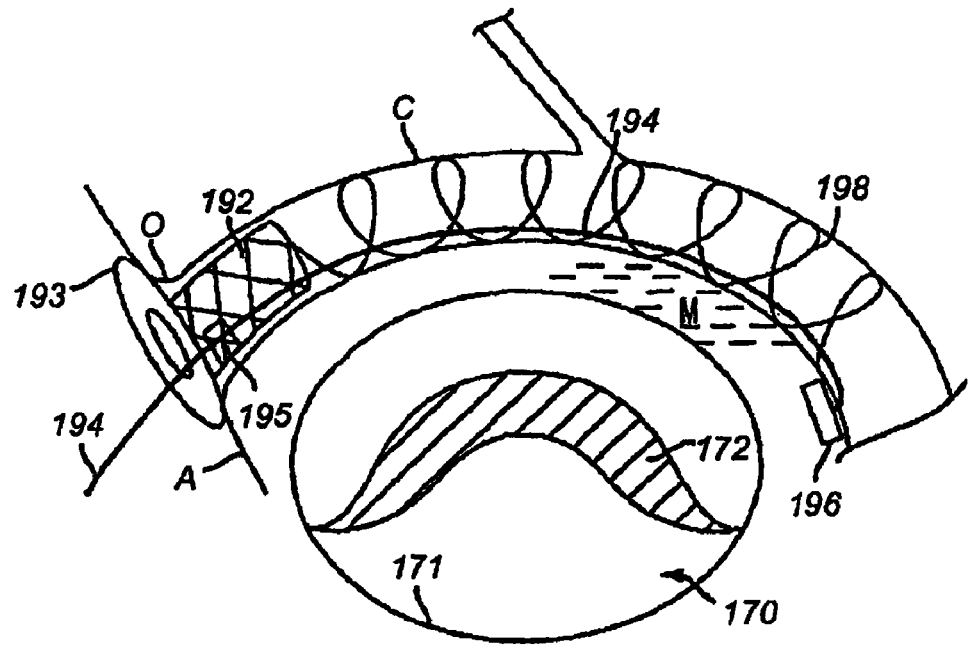
FIGS. 43A-43B illustrate deployment and actuation of the device of FIGS. 42A-42C.
Figure 43B:
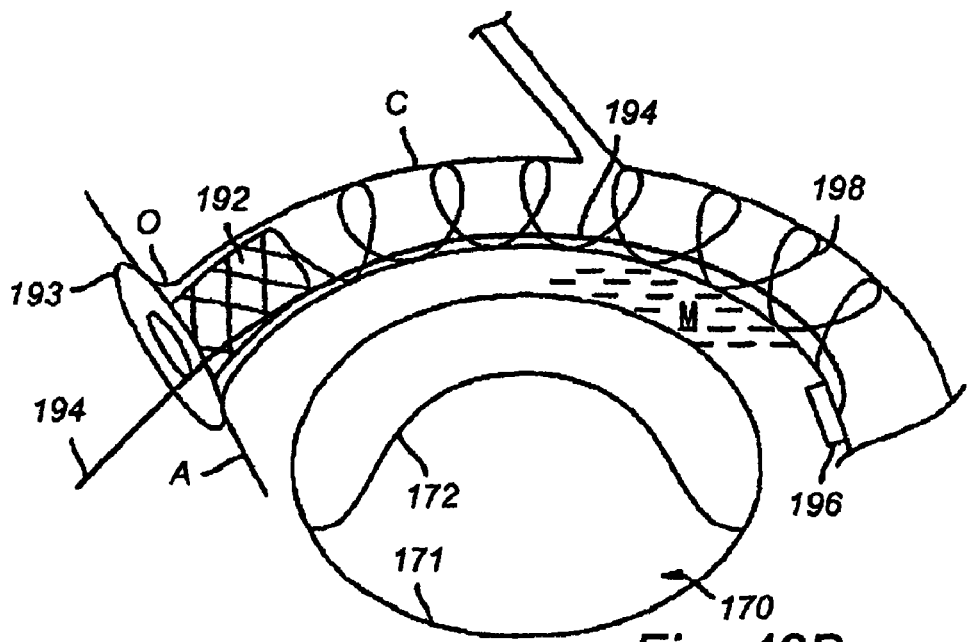

Referring to FIGS. 43A and 43B, device 190 of FIG. 42 is illustrated in a deployed state to treat mitral insufficiency. Flange 193 is deployed abutting coronary ostium O, e.g., within right atrium A. Proximal stent section 192 and optional coil section 198 are deployed within the coronary sinus and great cardiac vein C. Distal anchor 196 is disposed within myocardium M, or alternatively, may extend into the left ventricle or another suitable region, as will be obvious to those skilled in the art. It should further be appreciated to those skilled in the art that while anchor 196 is illustrated as a cylindrical bar, it may comprise square, circular or other configurations, e.g., a plurality of barbs.

The proximal end of wire 194 extends through cinch mechanism 195 and is manipulated to impose tension on wire 194, thereby reducing the distance between proximal stent section 192 and distal anchor 196. This in turn reduces the circumference of coronary sinus C accordingly, as shown in FIG. 43B. Upon completion of the procedure, i.e., when gap 172 is sufficiently closed, apparatus 200 is removed from the patient's vessel.

Advantageously, the use of distal anchor 196 is expected to reduce the shear stress imposed on coronary sinus C relative to the use of a proximal stent section alone as described for the embodiment of FIGS. 40A-40D and 41A-41B.

Figure 44A:
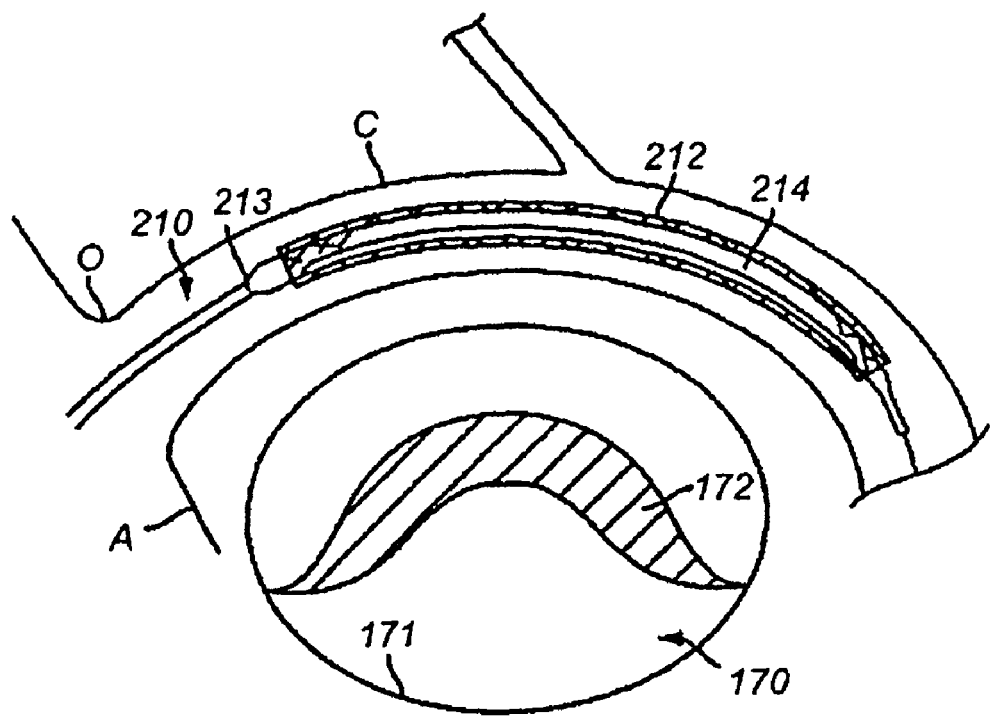
FIGS. 44A-44B illustrate another alternative embodiment of the device of the present invention comprising a balloon-expandable device that is deployed to a curved shape.
Figure 44B:
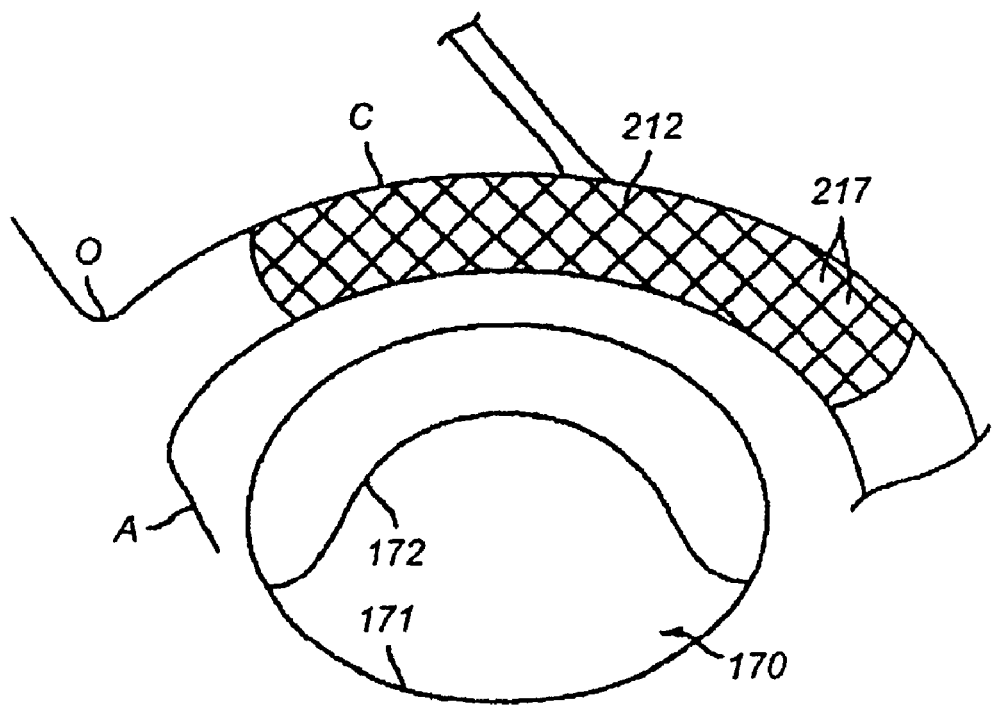

Referring now to FIGS. 44A-44B and 45A-45B, another embodiment of a device suitable for repairing mitral valve insufficiency is described. In this embodiment, device 210 comprises a balloon expandable stent 212, which may be tapered along its length. Stent 212 is disposed on the distal region of balloon catheter 213, which is capable of assuming a curved shape when inflated. As depicted in FIG. 44A, stent 212 and balloon catheter 213 are disposed in the patient's coronary sinus through the coronary ostium.

Once the position of stent 212 is determined, for example, by fluoroscopy, balloon 214 is inflated to expand the balloon 214 to its predetermined curved shape. Inflation of balloon 214 causes stent 212 to be plastically deformed in accordance with the predetermined shape of balloon 214. As will be of course be appreciated, the degree of mitral valve regurgitation may be monitored during the step of inflating balloon 214, so that stent 212 applies only so much compressive load on the mitral valve annulus as is required to reduce the regurgitation to a clinically acceptable level:

Catheter 214 is removed from the patient's vessel upon completion of the stenting procedure.

Figure 45A:
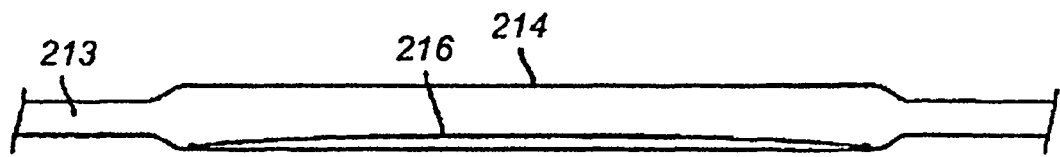
FIGS. 45A-45B illustrate a balloon that deploys to a predetermined curved shape.
Figure 45B:
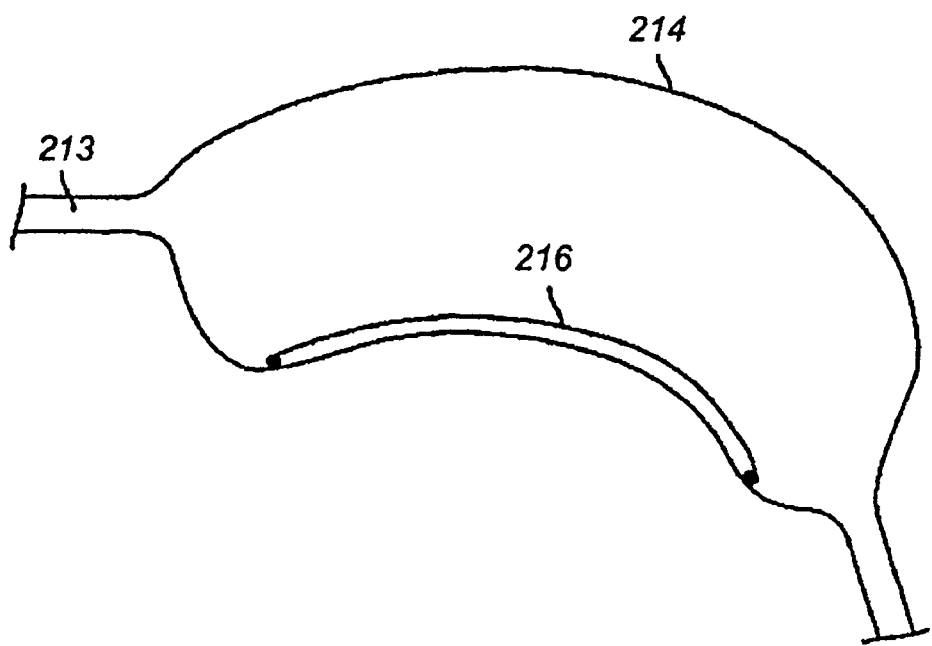

Referring to FIGS. 45A and 45B, the distal region of a balloon catheter suitable for use in the embodiment of FIG. 44 is described. The balloon catheter 213 has proximal and distal ends, and comprises balloon 214, and inflation lumen and guidewire lumens, as is per se known. In accordance with the principles of the present invention, balloon 214 includes an anchor element 216, such as a strand of wire, affixed to its interior surface, so that when the balloon is inflated, it adopts a predetermined shape, as shown in FIG. 45B. When deflated, balloon 214 assumes a straight configuration, shown in FIG. 45A, thus permitting stent 212 to be crimped to its outer surface.

Figure 46A:
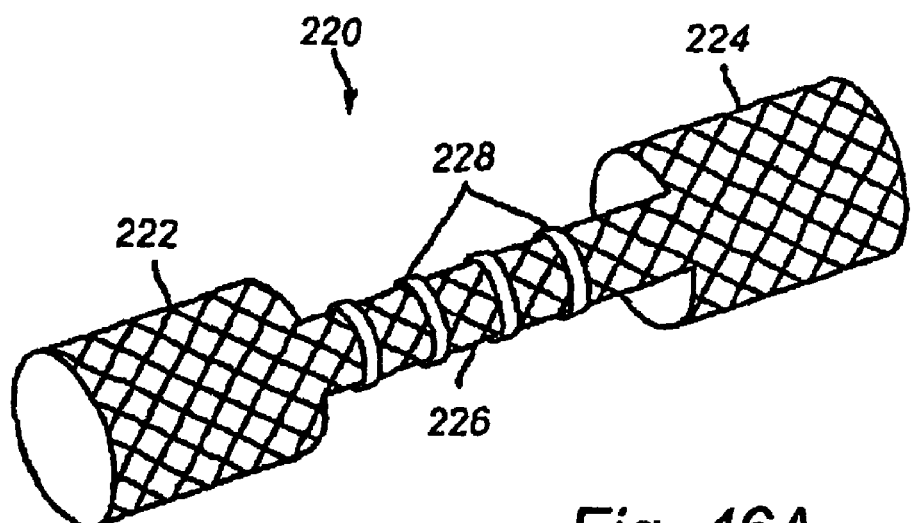
FIGS. 46A-46C are perspective and side views of a further alternative embodiment of a device of the present invention.
Figure 46B:
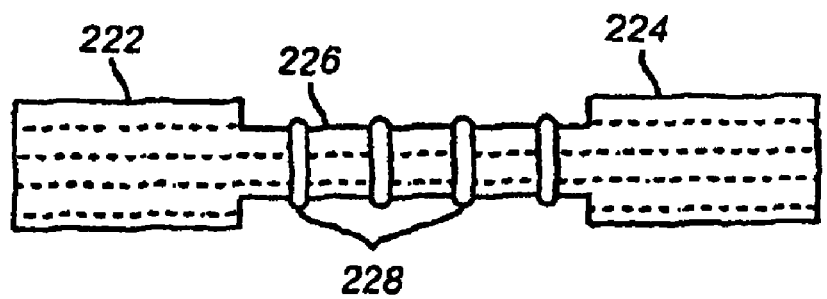
Figure 46C:
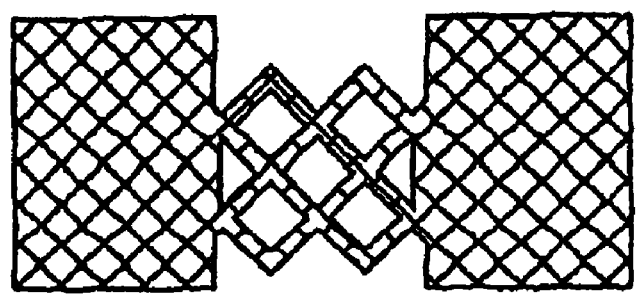

Referring now to FIGS. 46A-46C and 47A-47D, another alternative embodiment of the present invention is described, in which the device comprises proximal and distal stent sections joined by a central section capable of undergoing foreshortening. Device 220 comprises proximal stent section 222, distal stent section 224 and central section 226. Further in accordance with the principles of the present invention, device 220 includes one or more biodegradable structures 228, such as sutures, disposed on central section 226 to retain that section in the contracted shape for a predetermined period after placement of the device in a patient's vessel. In FIG. 46A, device 220 is depicted with its proximal and distal stent sections radially expanded, but with central section 226 restrained in the contracted position. FIG. 46B depicts device 220 with all three stent sections contracted as if disposed in a delivery catheter. FIG. 46C shows all three stent sections fully expanded.

In a preferred embodiment, all three sections are integrally formed from a single shape memory alloy tube, e.g., by laser cutting. The stent sections then are processed, using known techniques, to form a self-expanding unit. Device 220 has a contracted delivery configuration, wherein the device is radially contracted within a delivery sheath, and a deployed expanded configuration, wherein at least the proximal and distal sections self-expand to engage the interior surface of the coronary sinus or adjoining veins. Further in accordance with the present invention, the biodegradable structures may be designed to biodegrade simultaneously or at selected intervals.

Unlike the preceding embodiments, which may include either a proximal flange, distal anchor, or both, and which rely upon drawing the proximal and distal stent sections together at the time of deploying the device, this embodiment of the present invention permits the proximal and distal stent sections 222 and 224 to become biologically anchored in the venous vasculature before those sections are drawn together by expansion of central section 226 to impose a compressive load on the mitral valve annulus.

Figure 47A:
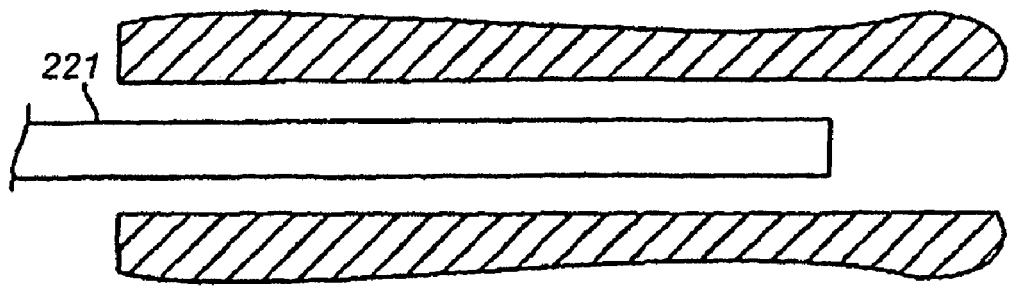
FIGS. 47A-47D illustrate deployment of the device depicted in FIGS. 46A-46C.
Figure 47B:
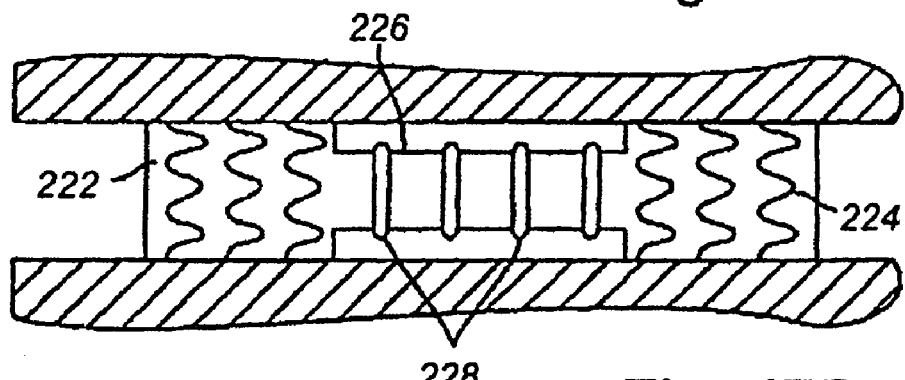
Figure 47C:
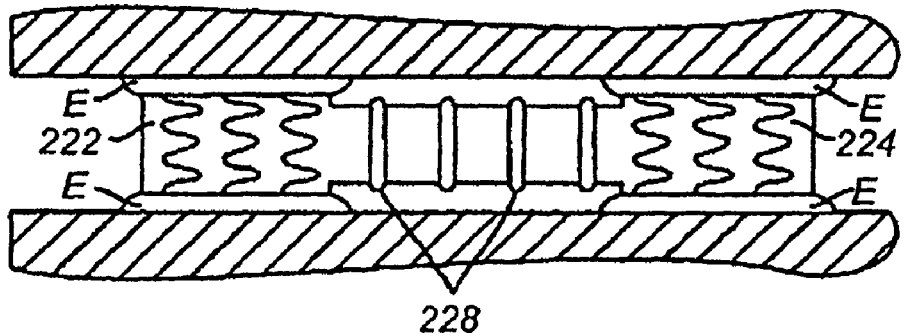

In particular, as depicted in FIGS. 47A-47C, device 220 is loaded into delivery sheath 221 and positioned within the patient's coronary sinus. The device is then ejected from the delivery sheath, so that the proximal and distal stent sections 222 and 224 radially expand into engagement with the vessel wall. At the time of deployment, central section 226 is retained in a contracted state by biodegradable structures 228, illustratively biodegradable sutures, e.g., a poly-glycol lactide strand or VICREL suture, offered by Ethicon, Inc., New Brunswick, N.J., USA.

Over the course of several weeks to months, the proximal and distal stent sections 222 and 224 will endothelialize, i.e., the vessel endothelium will form a layer E that extends through the apertures in the proximal and distal stent sections and causes those stent sections to become biologically anchored to the vessel wall, as depicted in FIG. 47C. This phenomenon may be further enhanced by the use of a copper layer on the proximal and distal stent sections, as this element is known to cause an aggressive inflammatory reaction.

Figure 47D:
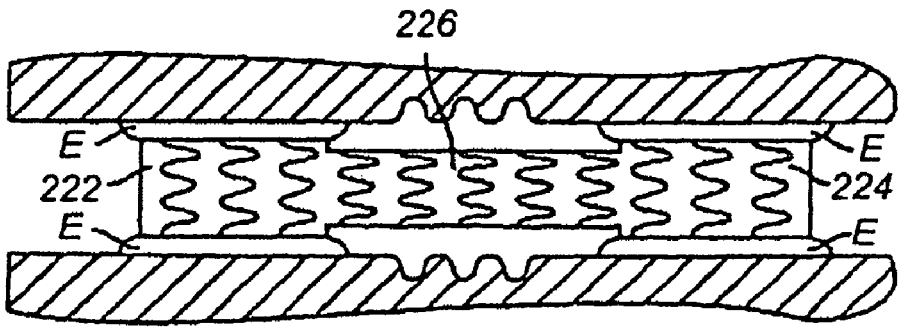

Over the course of several weeks to months, and preferably after the proximal and distal stent sections have become anchored in the vessel, biodegradable structures 228 that retain central section 226 in the contracted state will biodegrade. Eventually, the self-expanding force of the central section will cause the biodegradable structures to break, and release central section 226 to expand. Because central section 226 is designed to shorten as it expands radially, it causes the proximal and distal stent sections 222 and 224 of device 220 to be drawn towards one another, as shown in FIG. 47D. The compressive force created by expansion of central section 226 thereby compressively loads, and thus remodels, the mitral valve annulus, as depicted.

As suggested hereinabove, biodegradable structures 228 may be designed to rupture simultaneously, or alternatively, at selected intervals over a prolonged period of several months or more. In this manner, progressive remodeling of the mitral valve annulus may be accomplished over a gradual period, without additional interventional procedures. In addition, because the collateral drainage paths exist for blood entering the coronary sinus, it is possible for the device to accomplish its objective even if it results in gradual total occlusion of the coronary sinus.

Figure 48A:
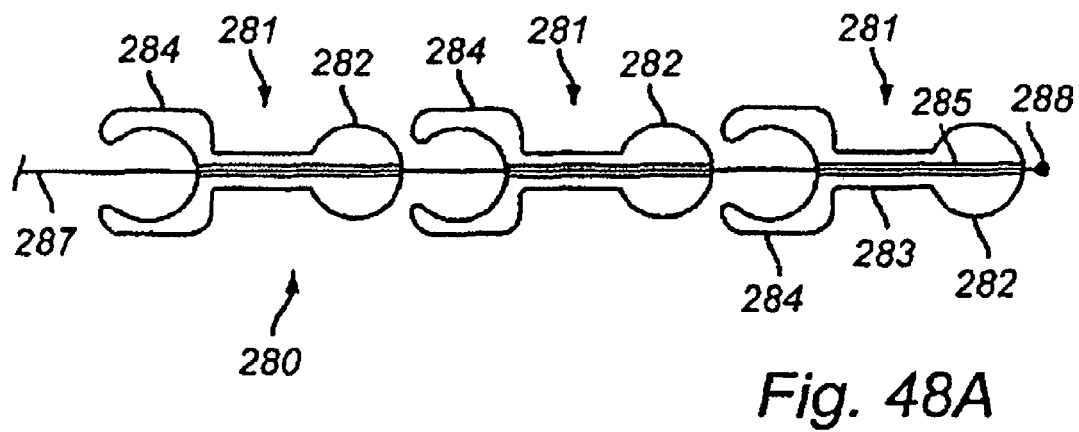
Figure 48B:
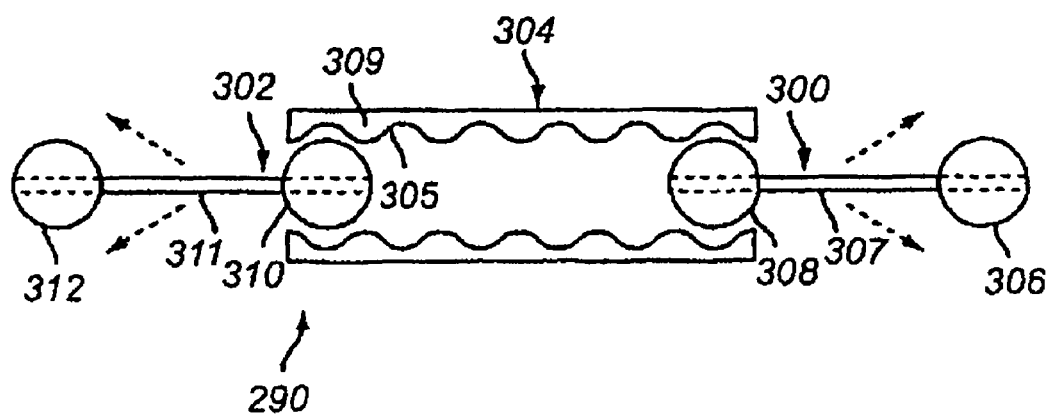

Referring now to FIGS. 48A-48B, another alternative embodiment of the present invention is described. In FIG. 48A, apparatus 280 comprises a plurality of interlocking segments 281. Each interlocking segment 281 preferably comprises a proximal section having socket 284, a distal section having ball 282, and a central section 283 extending therebetween. Each interlocking segment 281 further comprises lumen 285 configured to permit cinch wire 287 to pass through lumen 285. Cinch wire 287 having proximal and distal ends preferably comprises ball 288 affixed to the distal end so that ball 288 engages a distalmost interlocking segment 281 when retracted proximally. The retraction of cinch wire 287 enables a ball 282 to interlock with a socket 284 of an adjacent segment 281.

Apparatus 280 of FIG. 48A preferably is used in combination with apparatus 290 of FIG. 48B. A preferred use of apparatus 280 and 290 in combination is described in FIG. 50 hereinbelow. Apparatus 290 comprises proximal ball segment 302, distal ball segment 300, and connecting segment 304 having a plurality of sockets 305 separated by humps 309. Proximal ball segment 302 comprises proximal and distal ball segments 312 and 310, respectively, each having lumens extending therethrough, and hollow rod 311 extending therebetween. Similarly, distal ball segment 300 comprises proximal and distal balls 308 and 306, respectively, each having lumens extending therethrough, and hollow rod 307 extending therebetween. Distal ball 310 of proximal segment 302 initially is configured to engage the most proximal socket 305 within connecting segment 304, while proximal ball 308 of distal segment 300 initially is configured to engage a distalmost socket 305.

Proximal and distal ball segments 302 and 300 are capable of relative rotational and telescoping movement. Such movement may be achieved using a cinch wire configured to pass through each segment 300 and 302, as shown in FIG. 49A. In FIG. 49A, cinch wire 318 comprises distal ball 320 that is larger than a lumen of hollow rod 307 and is configured to abut distal ball 306 when a proximal end of cinch wire 318 is retracted proximally. Cinch wire 318 preferably is used in combination with push tube 316 that may stabilize or distally advance proximal segment 302.

By varying the maneuvers of push tube 316 and cinch wire 318, a range of telescoping and rotational motions between proximal and distal segments 302 and 300 may be achieved, as shown in FIG. 49B. In FIG. 49B, a push force applied to ball 312 allows ball 310 to overcome the resistive forces provided by hump 309. As illustrated, the push force applied to ball 312 has advanced proximal segment 302 by two sockets relative to distal segment 300. Also, as shown in FIG. 49B, distal segment 300 has been retracted by one socket with respect to proximal segment 302, e.g., by proximally retracting cinch wire 318. Ball 308 also has been rotated at an angle, which in turn rotates distal segment 200 with respect to proximal segment 302.

Referring to FIG. 49C, an alternative method for providing relative telescoping and rotational motion for apparatus 290 of FIG. 48B is described. Apparatus 290 further comprises push tube 316 and wire loop 325. Wire loop 325 extends through a lumen within proximal and distal segments 302 and 300, then loops around the distal end of distal segment 300 and back into opening 327 of push tube 316. A physician then may manipulate a proximal portion of wire loop 325 to provide a range of telescoping or rotational motions between proximal and distal segments 302 and 300.

Figure 50:
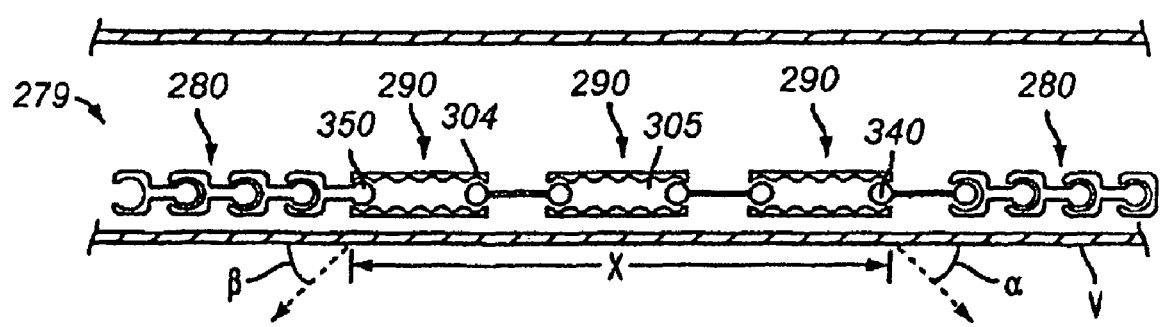

Referring now to FIG. 50, a combination of apparatus 280 and apparatus 290 are used to provide a range of motion within vessel V, e.g., the coronary sinus. As described hereinabove, the present invention aims to treat mitral insufficiency by shortening the radius of curvature of the coronary sinus, which in turn applies a compressive force upon the mitral valve. In FIG. 50, the combination of apparatus 280 and apparatus 290 first may engage a wall of vessel V, e.g., via barbs or hooks (not shown) affixed to apparatus 280 and 290, and then the relative telescoping or rotational motion of segments may be used to bend vessel V to apply a compressive load on the mitral valve annulus.

In a preferred embodiment, mitral insufficiency apparatus 279 comprises a proximal and distal section comprising apparatus 280, and a plurality of sections comprising apparatus 290 disposed therebetween. Cinch wire 318 and push tube 316 of FIGS. 49A-49B preferably are used to manipulate relative rotational and telescopic motion of all of the components. In a first preferred step, the balls of apparatus 280 are coupled to their respective sockets, e.g., by proximally retracting cinch wire 318. Then, in a next step, balls 340 and 350 which connect apparatus 280 to apparatus 290 are rotated within sockets of connective segment 304 to allow apparatus 280 to be angled relative to apparatus 290 by angles .alpha. and .beta., as illustrated in FIG. 50. This in turn applies a desired compressive load on the mitral valve annulus. Then, in a final step, the balls of apparatus 290 may be advanced incrementally in a longitudinal direction within sockets 305 of connective segments 304 to reduce distance X. When vessel V is the coronary sinus, reducing the distance X will apply a compressive force to the mitral valve to treat mitral insufficiency.

While preferred illustrative embodiments of the invention are described above, it will be apparent to one skilled in the art that various changes and modifications may be made therein without departing from the invention. The appended claims are intended to cover all such changes and modifications that fall within the true spirit and scope of the invention.

The invention claimed is:

1. An apparatus for applying a compressive load on body tissue, the apparatus comprising:
   a catheter having proximal and distal ends and a lumen extending through the catheter;
   a balloon affixed to the catheter, the balloon being in fluid communication with the lumen and having contracted and deployed states, wherein the balloon assumes a predetermined shape in the deployed state, wherein the balloon includes an interior surface defining an expandable chamber; and
   a stent having contracted and deployed states, wherein the stent is plastically deformable by the balloon and substantially conforms to the predetermined shape of the balloon in the deployed state, wherein the stent is configured to apply a compressive load on surrounding body tissue when in the deployed state;
   wherein, in the deployed state, the balloon is maintained in the predetermined shape, at least in part, by an anchor element extending along a constrained portion of the interior surface of the balloon and limiting expansion of the balloon in the constrained portion in comparison with expansion in an unconstrained portion in which the anchor element is not present when the balloon changes from its contracted to its deployed state, wherein an entirety of the anchor element is disposed within the expandable chamber of the balloon.

2. The apparatus of claim 1, wherein the balloon assumes a curved shape in the deployed state.

3. The apparatus of claim 1, wherein, when the balloon is in the deployed state, the anchor element is curved along the interior surface of the balloon.

4. The apparatus of claim 1, wherein, when the balloon is in the contracted state, the anchor element is substantially straight along the interior surface of the balloon.

5. An apparatus for applying a compressive load on body tissue, the apparatus comprising:
  an elongate delivery member having proximal and distal ends and a lumen extending through the elongate delivery member;
  a balloon affixed to the elongate delivery member, the balloon being in fluid communication with the lumen and having contracted and deployed states, wherein the balloon assumes a predetermined shape in the deployed state, wherein the balloon includes an interior surface defining an expandable chamber;
  an elongate member having first and second states, wherein the elongate member is plastically deformed from the first state to the second state by the balloon when the balloon changes from the contracted state to the deployed state;
  wherein the elongate member substantially conforms to a surface of the balloon in the deployed state, wherein the elongate member is configured to apply a compressive load on adjacent body tissue when in the second state;
  wherein, in the deployed state, the balloon is maintained in the predetermined shape, at least in part, by an anchor element extending along a constrained portion of the interior surface of the balloon that restrains expansion of the balloon in the constrained portion in comparison with expansion in an unconstrained portion of the balloon in which the anchor element is not present; and
  wherein an entirety of the anchor element is disposed within the expandable chamber of the balloon.

6. The apparatus of claim 5, wherein the balloon comprises a curved shape in the deployed state.

7. The apparatus of claim 5, wherein, when the balloon is in the deployed state, the anchor element is curved along the interior surface of the balloon.

8. The apparatus of claim 5, wherein, when the balloon is in the contracted state, the anchor element is substantially straight along the interior surface of the balloon.

* * * * *

UNITED STATES PATENT AND TRADEMARK OFFICE
CERTIFICATE OF CORRECTION

PATENT NO.        : 8,075,616 B2                                                Page 1 of 1
APPLICATION NO.   : 10/500188
DATED             : December 13, 2011
INVENTOR(S)       : Jan O. Solem et al.

It is certified that error appears in the above-identified patent and that said Letters Patent is hereby corrected as shown below:

On the title page item [75] should read:

Jan Otto Solem, Stetten (CH); Per Ola Kimblad, Lund (SE); Randolf von Oepen, Los Altos Hills, CA (US); Bodo Quint, Rottenburg-Seebronn ~~(SE)~~ (DE); Gerd Seibold, Ammerbuch ~~(SE)~~ (DE); Kenneth J. Michlitsch, Livermore, CA (US); Suk-Woo Ha, Langwiesen (CH); Karl-Ludwig Eckert, Marthalen (CH); Ib Joergensen, Haigerlock (DE); Stevan Nielsen, Rottenburg (DE)

Signed and Sealed this
Seventh Day of August, 2012

David J. Kappos
*Director of the United States Patent and Trademark Office*